US010365220B2

(12) United States Patent
Chan et al.

(10) Patent No.: US 10,365,220 B2
(45) Date of Patent: Jul. 30, 2019

(54) SINGLE-CELL RAMAN SPECTROSCOPY FOR THE NON-DESTRUCTIVE, NON-INVASIVE ANALYSIS OF CELLS AND CELLULAR COMPONENTS

(75) Inventors: James W. Chan, Davis, CA (US);
Thomas R. Huser, Davis, CA (US);
Stephen M. Lane, Davis, CA (US);
John C. Rutledge, Davis, CA (US);
Douglas S. Taylor, Davis, CA (US);
Theodore Zwerdling, Davis, CA (US);
Ronald Li, Davis, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 1635 days.

(21) Appl. No.: 11/916,273

(22) PCT Filed: May 31, 2006

(86) PCT No.: PCT/US2006/021186
§ 371 (c)(1),
(2), (4) Date: Feb. 22, 2010

(87) PCT Pub. No.: WO2006/130728
PCT Pub. Date: Dec. 7, 2006

(65) Prior Publication Data
US 2010/0241357 A1 Sep. 23, 2010

Related U.S. Application Data

(60) Provisional application No. 60/686,370, filed on May 31, 2005.

(51) Int. Cl.
*G01N 33/48* (2006.01)
*G01N 21/65* (2006.01)
*G01J 3/44* (2006.01)
*G06G 7/58* (2006.01)

(52) U.S. Cl.
CPC ............... *G01N 21/65* (2013.01); *G01J 3/44* (2013.01); *G01N 2021/656* (2013.01)

(58) Field of Classification Search
None
See application file for complete search history.

(56) References Cited

U.S. PATENT DOCUMENTS

| 4,893,886 | A | | 1/1990 | Ashkin et al. |
| 5,733,739 | A | * | 3/1998 | Zakim et al. .................. 435/29 |
| 5,991,653 | A | | 11/1999 | Richards-Kortum et al. |
| 6,067,859 | A | | 5/2000 | Kas et al. |
| 6,139,831 | A | | 10/2000 | Shivashankar et al. |
| 6,281,971 | B1 | | 8/2001 | Allen et al. |
| 6,642,012 | B1 | | 11/2003 | Ashdown |
| 6,833,542 | B2 | | 12/2004 | Wang et al. |
| 2004/0012778 | A1 | | 1/2004 | Li et al. |
| 2004/0063216 | A1 | | 4/2004 | Lubocki |
| 2005/0048581 | A1 | | 3/2005 | Chiu et al. |
| 2005/0069900 | A1 | | 3/2005 | Lentrichia |

FOREIGN PATENT DOCUMENTS

WO  WO 2004/008121 A2  1/2004

OTHER PUBLICATIONS

PCT International Search Report and Written Opinion, PCT/US06/21186, dated Apr. 30, 2007, 10 pages.
Deinum, G. et al., "Histological Classification of Raman Spectra of Human Coronary Artery Atherosclerosis Using Principal Component Analysis," Applied Spectroscopy, 1999, pp. 938-942, vol. 53, No. 7.
Notingher, I. et al., "In Situ Spectral Monitoring of mRNA Translation in Embryonic Stem Cells During Differentiation in Vitro," Anal. Chem., 2004, pp. 3185-3193, vol. 76.
Puppels, G.J. et al., "Studying Single Living Cells and Chromosomes by Confocal Raman Microspectroscopy," Nature, Sep. 20, 1990, pp. 301-303, vol. 347, No. 6290.

* cited by examiner

Primary Examiner — Eric S Dejong
(74) Attorney, Agent, or Firm — Fenwick & West LLP

(57) ABSTRACT

Raman spectra of cells, such as normal human T- and B-cells from peripheral blood or human tonsil and the corresponding transformed cells are obtained by optically trapping the cells and obtaining their Raman spectra. The trapped cells can be subjected to one, two, or more different excitation wavelengths, and each wavelength of the corresponding Raman spectra can be stored in a separate channel. In preferred embodiments, two spectra are subtracted from each other to give a difference spectrum and each channel is analyzed independently to characterize the trapped cell. Alternatively, the Raman spectrum can be subjected to Principal Component Analysis (PCA) in order to characterize the trapped cell. The trapped cell thus classified can be sorted, or further manipulated.

22 Claims, 12 Drawing Sheets

SINGLE-CELL RAMAN SPECTROSCOPY FOR THE NON-DESTRUCTIVE, NON-INVASIVE ANALYSIS OF CELLS AND CELLULAR COMPONENTS

CROSS REFERENCE OF RELATED APPLICATIONS

This application is the National Stage of International Application No. PCT/US2006/021186, published in English under PCT Article 21(2), filed May 31, 2006, which claims the benefit of U.S. Provisional Application Ser. No. 60/686,370, filed on May 31, 2005, both of which are incorporated by reference in their entirety.

GOVERNMENT INTEREST

This invention was made with support of government grants PHY-012099 from the National Science Foundation, and W-7405-Eng-48 from the U.S. Department of Energy. Therefore, the United States government may have certain rights in the invention.

FIELD OF INVENTION

The present invention relates to optical methods and systems for the diagnosis of diseases and for the characterization of cells and cellular components.

BACKGROUND

A major problem in the treatment of cancer remains its early detection. Early detection enables therapeutic treatment from the onset of the disease resulting in successful treatment in many cases. Current methods for detection and quantitation of neoplastic cells employ a combination of techniques such as histochemical stains, exogenous labeling of surface markers, or light microscopy for morphological cell characterization for cancer cell recognition. These techniques are time consuming and are not very accurate, as a high number of false positive results can be obtained.

Raman microspectroscopy has been used for detection and identification in various scientific disciplines, including materials science, biology and medicine. G. Turrell and J. Corset, Raman microscopy, (Academic Press, London, 1996). Raman microspectroscopy uses a focused laser beam to illuminate particles, and the resulting scattered light is detected and analyzed. The incident light on the sample excites molecules in the sample to produce elastic scattering and inelastic scattering. The inelastically scattered light spectrum is called a Raman spectrum. The molecular composition and structure information of the particles can be obtained from positions, intensities, and line-widths of the Raman peaks in the spectra. One difficulty associated with Raman spectroscopy is the very low signal intensity which is inherent to Raman scattered light. It is well known that the scattered light intensity scales with the frequency raised to the fourth power. The weak Raman signal must be distinguished from Rayleigh scattered light, which is elastically scattered light of the same frequency as the incident light and which constitutes a much greater fraction of the total scattered light. The Raman signal can be separated from Rayleigh scattered light through the use of filters, gratings, or other wavelength separation devices, however, this can have the effect of further weakening the measured Raman signal through the additional attenuation which can occur when the light passes through a wavelength separation device.

Puppels demonstrated the use of confocal Raman microspectroscopy on a single cell (Puppels et al. (1990) Nature 347:301-303). The method has had many applications for biological studies, including the use of the technique as a potential diagnostic tool for cancer detection. Raman spectroscopy of tissue and cells, which can provide detailed molecular information about the DNA, protein, lipid, and carbohydrate content, has been suggested as a diagnostic tool for cancer detection. For example, Raman spectra studies of squamous dysplasia, a precursor to cervical cancer, classified high-grade dysplasia from all others based on the observed increases in the intensity ratios of 1454 $cm^{-1}$ to 1656 $cm^{-1}$ and decreases in the intensity ratio of 1330 $cm^{-1}$ to 1454 $cm^{-1}$ for the squamous dysplastic tissues. These peaks were assigned to collagen, phospholipids, and DNA. Tumor and normal bronchial tissue can be classified based on observed higher Raman signals from nucleic acids, typtophan, phenylalanine, and lower signals from phospholipids, proline, and valine in tumor tissue. Specifically, peaks ascribed to nucleic acid at 1223 $cm^{-1}$ and 1335 $cm^{-1}$ increase, peaks ascribed to collagen/phospholipid at 1302 $cm^{-1}$ and 1405 $cm^{-1}$ decrease, tryptophan and phenylalanine peaks such as 1618 $cm^{-1}$ and 1602 $cm^{-1}$, respectively, increase. Thus, Raman spectroscopy can be used to characterize diseases.

Optical trapping using a single laser beam, first pioneered by Ashkin et al. in 1986, utilizes single photons of light to impart radiation pressure forces on a particle. It has been shown that when a laser source is tightly focused, it is possible to generate both radiation axial scattering forces and transverse gradient forces to draw a particle towards the center of the beam into a stable trap at the laser focus. "Optical tweezers" have been used as a biological tool for the manipulation of single biological species, including manipulation of bacteria, viruses, single cells, subcellular organelles, single motor proteins, and single DNA molecules.

Recently, optical trapping combined with confocal Raman spectroscopy for simultaneously probing the molecular information of the trapped particle using a single laser source has attracted increased interest in the biophysical study of the molecular changes in the subcellular components of single live cells over an extended period of time. Confocal Raman microspectroscopy has been shown to provide information on the DNA, protein, and lipid constituents of a live biological cell with distinct bands assignable to nucleotide bases, amide, and others. The PCT publication, WO 2004/008121 by Li and Dinno, shows that an optical trap for cells combined with Raman spectroscopy can be used to distinguish between live yeast and microbial cells and unstained dead yeast and microbial cells. U.S. Pat. No. 6,067,859 to Kas et al. discloses an "optical stretcher" where a tunable laser is used to trap and deform cells between two counter-propagating beams generated by a laser. The system is utilized to detect single malignant cancer cells.

The combination of optical trapping with Raman spectroscopy has the advantages of 1) enabling the study of micro and nano particles in solution over an extended period of time that might otherwise not be able to be probed due to their constant Brownian motion in solution, 2) maximizing Raman signal collection, and 3) probing of natural suspension of cells.

There is a need for diagnostic methods and apparatus involving a single rapid technique that can accurately and non-invasively identify and sort single cancerous cells, such as leukemic cells, from healthy cells for the diagnosis and treatment of cancers in a clinical setting.

SUMMARY

The present invention provides methods and apparatuses for classifying cells and for detecting abnormal cells. The invention optically traps individual cells in solution using laser tweezers and obtains Raman spectrum from the cell, different areas of the same cell, and different cells within the same cell subpopulation. The spectra are normalized and compared using statistical techniques. The optically trapped cells can be classified based on their Raman spectra and further manipulated.

In one aspect, the invention provides methods for detecting an abnormal cell in a sample by trapping a single cell from the sample in an optical trap, illuminating the trapped cell with electromagnetic radiation wherein a Raman spectrum is produced, and analyzing the Raman spectrum to determine if the trapped cell is abnormal. The sample can comprise a red blood cell or one white blood cell, such as T-lymphocyte or a B-lymphocyte. The white blood cell can be a normal cell or an abnormal cell, such as a lymphoma cell, a leukemia cell, or a myeloma cell. In one aspect, a plurality of Raman spectra of the same trapped cell is obtained using two, three or four excitation wavelengths, wherein the excitation wavelengths are separated by approximately 1 nm to about 50 nm, such as by 1 nm, 2 nm, 3 nm, 4 nm, or 5 nm. The first Raman spectrum can be obtained at the first excitation wavelength and a second Raman spectrum can be obtained at a second excitation wavelength, and the first spectrum is subtracted from the second spectrum to provide a difference spectrum. In another aspect, the Raman spectrum is stored in a multitude of channels wherein each channel stores a single wavelength, and wherein each channel is subjected to statistical analysis individually.

These and other aspects of the present invention will become evident upon reference to the following detailed description. In addition, various references are set forth herein which describe in more detail certain procedures or compositions, and are therefore incorporated by reference in their entirety.

BRIEF DESCRIPTION OF DRAWINGS

FIG. 6b shows a plot of PC1 v. PC2 for Raji cells and B cells. FIG. 6c shows a plot of PC1 v. PC2 for Jurkat, Raji, T- and B-cells.

FIGS. 7c, 7d, and 7e are the loading values of each channel for T-cell versus Jurkat cell, B-cell versus Raji cell, and T-cell versus B-cell versus Jurkat versus Raji cell, respectively. Also shown in FIG. 7 (a, b) are the difference spectra of T-cell versus Jurkat cell and B-cell versus Raji cell, respectively. Increased positive or negative deviation from baseline indicates greater contribution to the PC.

DETAILED DESCRIPTION

I. Definitions

Figure 1:
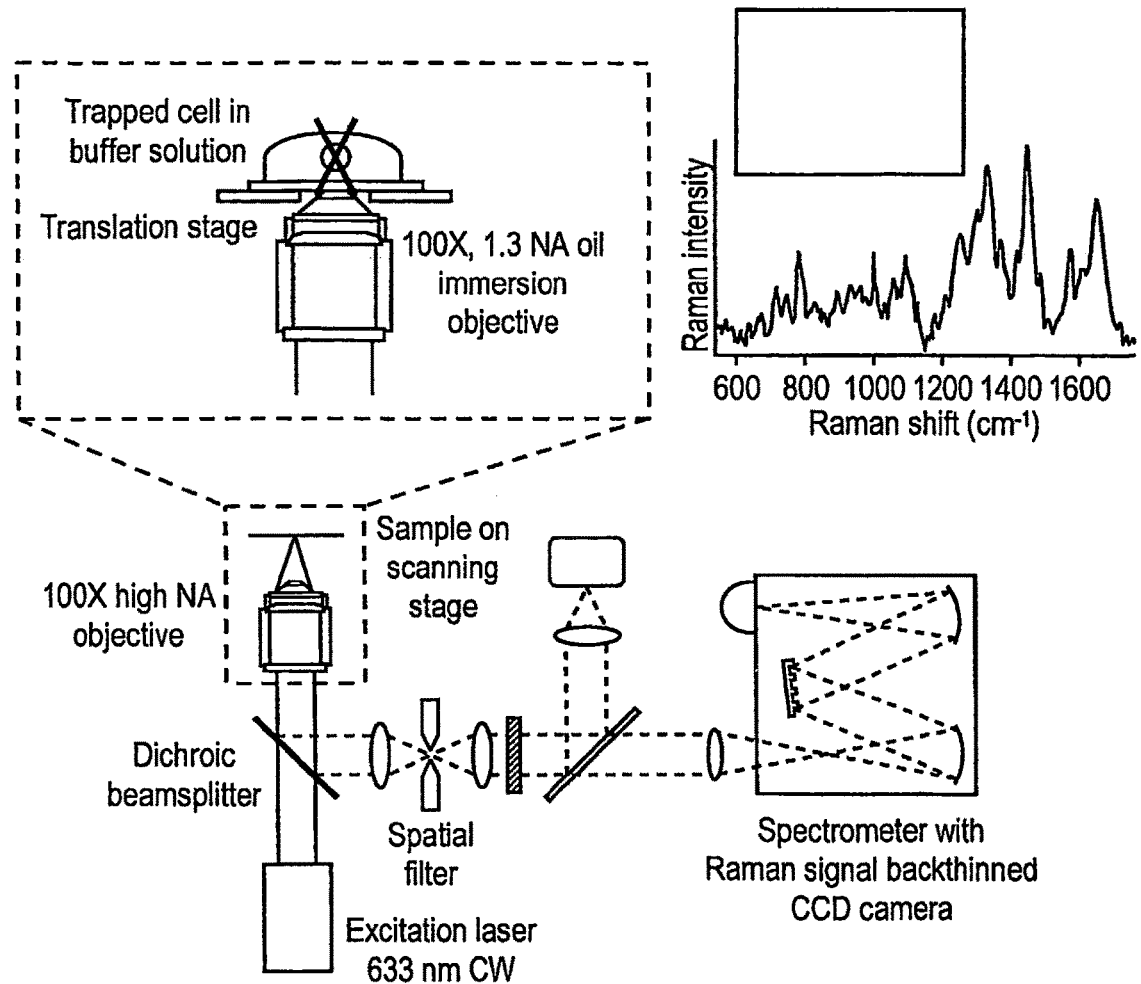
FIG. 1 illustrates the experimental confocal micro-Raman setup used for the spectroscopic analysis of individual normal T and B cells and their transformed counterparts, Jurkat and Raji cells. Also shown is a white light microscope image of a single trapped T cell and a background corrected Raman spectrum of one T cell acquired over 3 minutes.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise.

All publications, patents and patent applications cited herein, whether supra or infra, are hereby incorporated by reference in their entirety.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

As used herein, the term "cancer" refers to cell proliferation, including solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, merkel cell, mucinous, non-small cell lung, oat cell, papillary, scirrhous, bronchiolar, bronchogenic, squamous cell, and transitional cell), histiocytic disorders, leukemia (e.g., b-cell, mixed-cell, null-cell, T-cell, T-cell chronic, HTLV-II-associated, lyphocytic acute, lymphocytic chronic, mast-cell, and myeloid), histiocytosis malignant, Hodgkin's disease, immunoproliferative small, non-Hodgkin's lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyo sarcoma, myoblastoma, myoma, myosarcoma, rhabdomyoma, rhabdomyosarcoma, ependymoma, ganglioneuroma, glioma, medulloblastom a, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's, Kaposi's, and mast-cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia).

II. Overview

Individual cells can be trapped in solution by optical trapping. The trapped cells can then be characterized by Raman spectroscopy. The spectra in the fingerprint region can be obtained, and each wavelength can be stored as a single channel. The data in each channel can be independently normalized and each channel can be subjected to statistical analysis independently. The difference spectra between the normal cell and the cell under investigation can be used to determine if the cell under investigation is normal or neoplastic. Further, the Raman Spectrum can be analyzed using Principal Component Analysis (PCA), and the cells can be characterized based on their biomolecular and biochemical signatures. The cell thus characterized can be further manipulated, such as, for example, sorted and separated into normal or neoplastic cell, destroyed, and the like.

III. Optical Trap

In one aspect, a single cell or a virus, or a collection of cells, can be trapped in an optical trap. Typical apparatus for use in the practice of the invention is shown in FIG. 1. The cell can be a single cell organism, such as a bacterial, a yeast, and the like, or it can be obtained from a subject such as plant, fish, animal, and the like. For example, the cells from the subject can be a normal cell, a cancer cell, a fetal stem cell, an adult stem cell, an activated B or T cell, a dentritic cell, a hypoxanthine-guanine phosphoribosyltransferase (HPRT) cell, or cellular organelles, such as, mitochondria, nucleus, endoplasmic reticulum, microsomes, and the like. Representative white blood cells include polymorphonuclear cells (PMNs), monocytes, T-lymphocytes and B-lymphocytes. Some representative white blood cell malignancies include lymphomas, leukemias, and myelomas. Other white blood cell malignancies are known in the art.

The cell can be manipulated by optical trapping, also referred to as the use of "optical tweezers," as known in the art. The principle behind optical trapping is that light carries momentum which can be expressed as radiation pressure. When light is absorbed, reflected, or refracted by a material, such as a cell, momentum is transferred to the material. Optical tweezers have been developed that controllably deliver radiation pressure to manipulate small particles. Exemplary applications of optical tweezer technology include the manipulation of biological particles, such as cells, bacteria, and viruses (U.S. Pat. No. 4,893,886 to Ashkin et al. and U.S. Pat. No. 6,067,859 to Kas et al.), and the immobilization of biomolecules such as DNA, RNA, proteins, lipids, carbohydrates, or hormones (see U.S. Pat. No. 6,139,831 to Shivashankar et al.).

The light source for use with the methods of the present invention preferably avoids damage to biological materials, such as cells. By choosing wavelengths in ranges where the absorption by cellular components, mostly water, is minimized, the deleterious effects of heating can be minimized. Thus, to avoid excessive heating or photodamage, the light is preferably in the infrared range. Thus, the light used can have wavelengths in the range from approximately 0.3 µm to approximately 1.8 µm, and more preferably, from about 0.8 µm to about 1.8 µm. However, a light having a wavelength generally considered to be damaging to biological materials can be used, such as where the illumination is for a short period of time where deleterious absorption of energy does not occur.

Generally, the light sources will be coherent light sources. Typically, the coherent light source will consist of a laser. However, non-coherent sources may be utilized, provided the system can generate the forces required to achieve optical trapping. Various laser modes may be utilized, such as the Laguerre-Gaussian mode of the laser. Furthermore, if there is more than one light source in the system, these sources can be coherent or incoherent with respect to each other. One such laser is Nd:YAG, a solid-state four-level laser which utilizes a YAG crystal with Neodymium (Nd) impurity ions. YAG (yttrium aluminum garnet) crystal lasers can produce output powers up to a kilowatt. Other suitable lasers include diode lasers in the near infrared region (780-950 nm) for low power and titanium-sapphire laser. The diode lasers can be made of such materials as GaAlAs, GaAs, InGaAlP, GaInP, AlGaAs, AlGaInP, GaAlP, InGaAsP, GaInP/AlInP, InGaP/InGaAlP, or GaInP/AlGaInP. For example, the GaAlAs diode (Diolite 800, LiCONix, California) emits light at wavelengths in the region of 780-800 nm, and the diode can be the Nd:YLF diode laser made by Spectra-Physics, and others can be used in the practice of the invention. Diode lasers are preferred because of their low power consumption and compact size. However, other continuous wave sources may be used, such as an argon laser, a Ti:sapphire laser, or a dye laser. Alternatively, a light emitting diode (LED) or super luminescent LED may be used.

The apparatus and methods of the present inventions utilize, at least in part, forces on particles caused by light. For example, a light pattern is moved relative to a substrate, the particle or cell, the medium containing the cell and/or the substrate supporting the cell and the medium, and the like. For example, the substrate may be formed from silica-based materials such as glass or quartz, or commercially available ceramic materials such as aluminum oxide, zirconium oxide, titanium oxide, and the like may be employed as well. By moving the light relative to cells, typically through a medium having some degree of viscosity, cells can be separated or otherwise characterized based at least in part upon the optical force asserted against the cells. Alternatively, the relative motion can be achieved by holding the light pattern stationary and moving the subject cells, medium and/or support structure relative to the optical pattern.

IV. Raman Spectra

A Raman spectroscopy apparatus includes a light source for generating at least one illumination wavelength of electromagnetic radiation selected to cause the trapped cell to emit a Raman spectrum comprising a plurality of wavelengths, a Raman spectrum detector for detecting a plurality of peak intensities of the Raman spectrum, and optionally a computer that receives input generated by the Raman spectrum detector that compares each of the Raman spectrum of the cell with known normal cells to detect abnormalities.

The Raman spectrum can be measured over a range of wavelengths, such as, for example 500 $cm^{-1}$ to 2000 $cm^{-1}$. The spectrum of each sample can be integrated for 1 minute to about 30 minutes, preferably about 3 minutes to about 15 minutes. The acquisition time is dependent on the laser power used for Raman excitation. For each cell trapped in the optical trap, Raman spectra can be obtained using a single or a plurality of excitation wavelengths. The number of different excitation wavelengths can be from 1 to about 100, such as, for example, 2, 3, 4, 5, or 6, and any other integer. The plurality of excitation wavelengths can be separated by between 1 nm to about 100 nm, preferably about 1 nm to about 50 nm, or more preferably about 1 nm to about 10 nm, or any integer in between. Thus, for example, 2 excitation wavelengths can be used that are separated by 1 nm, 2 nm, 3 nm, 4 nm, 5 nm, and the like. For example, the first spectrum can be obtained using the excitation wavelength of 800 nm, and the second spectrum of the same trapped cell can be obtained using the excitation wavelength of 802 nm.

In one aspect of the invention, the light source for generating the Raman spectrum can be the same as the light source for optical trapping. The trapped cell can be illuminated with the laser light producing Raman scattering signals, and a Raman spectrum can be detected from the Raman scattering signals that are produced.

In another aspect of the invention, the Raman spectrum can be collected in the molecular fingerprint region from about 600 $cm^{-1}$ to about 1800 $cm^{-1}$. Each wavelength can be stored in a separate channel. Thus, for example, the Raman spectra in the fingerprint region can be stored in 1340 channels. The data in each channel can be individually analyzed, treated, or subjected to statistical analysis. For example, the data in each channel can be normalized individually by dividing the value in each channel by the total intensity of the Raman spectrum in all channels or to the intensity in one specific channel. In another aspect, the 99% confidence limits for each of the channels that make up the Raman spectrum can be calculated, and the average Raman spectrum for each cell can be plotted with the upper and lower limits for each channel. Comparison of the Raman spectra can be made, where differences can be used to indicate the cell type. In another aspect, a variability index for each channel can be calculated, where the 99% confidence limit for each channel is divided by the mean value. The variability index can be used to characterize the cell under investigation. In yet another aspect, a T-test can be administered to each channel in the Raman spectrum to confirm that the differences are significant.

In another aspect of the invention, a plurality of Raman spectra for each trapped cell can be obtained using a plurality of excitation wavelengths. The plurality of Raman spectra can be 2 spectra, 3 spectra, 4 spectra, or more, and the like, that can be obtained by using 2 different excitation wavelengths, 3 different excitation wavelengths, or 4 or more different excitation wavelengths, respectively. Preferably, two different Raman spectra are obtained using 2 different excitation wavelengths. The resulting Raman spectra are shifted with respect to each other, whereas the interfering background signals will remain constant in the plurality of Raman spectra. A difference spectrum can be obtained by subtracting the two or more spectra from each other where the difference spectrum will be substantially free of the background signal. The difference spectrum can then be analyzed.

Alternatively, the Raman spectrum or spectra of a plurality of cells for each cell type can be obtained. The plurality of cells can be 2 cells to about $10^5$ cells, preferably 2 cells to about $10^4$ cells, 2 cells to about 1000 cells, or 2 cells to about 100 cells, or any integer in between. The Raman spectra of the plurality of the cells can be averaged to provide an average Raman spectrum for the cell type. Similarly, the average Raman spectrum of a diseased cell, such as a cancer cell, can be obtained. A t-test can be performed on each channel of the average Raman spectrum for the normal cell type and the diseased cell and the channels with the greater significance p<0.01 (99% confidence level) can be selected and used for discriminating between cell types.

In yet another aspect of the invention, each wavelength of the Raman spectrum can be stored in a separate channel, and channels that are more significant for identification of the type of cell can be selected. Thus, instead of analyzing all 1340 channels, less than 1340 channels can be selected for analysis and comparison. The number of channels selected can be 1, 2, 3, 4, 5, 6, 7, 8, 9 10, 11, 12, 13, or any number of channels that is less than 1340. In one aspect, from 1 to about 200 channels can be selected, preferably from 1 to about 100 channels can be selected. The channels identified as more significant can be used to identify the type of cell in an unknown sample. For example, the significant channels for each type of cancer can be determined and stored in a database. Then, the significant channels for an unknown sample can be compared against the database, thereby identifying the cells in the unknown sample.

In another aspect of the invention, the Raman spectrum can be mapped to a reduced dimensionality by performing a Principal Component Analysis (PCA). PCA transforms the original variables of the Raman spectrum into a smaller set of linear combinations of the original variables called principal components that account for most of the variance of the original data set while maintaining as much information as possible of the original spectrum. Two spectra with similar meaning should map to a similar reduced-space representation (e.g. in a 2-D or 3-D graphical representation). This reduced dimensionality representation is useful for space-saving reasons, and for classification and comparison of cells and disease states since cells with similar biochemical and biomolecular signatures will map onto similar points. See, for example, Konstantinos Diamantaras and S. Y. Kung, "Principal Component Neural Networks: Theory and Applications", in the series "Adaptive and Learning Systems for Signal Processing, Communications, and Control", John Wiley & Sons, February 1996. Raman spectra of coronary artery tissue have been analyzed using PCA by Deinum et al. (Applied Spectroscopy 53: 938-942 (1999)), and test tissue samples were then characterized by comparing the principal components of the test samples with the known samples. Notingher et al. Anal. Chem. 76: 3185-3193 (2004) used PCA of Raman spectra to follow the differentiation of embryonic murine stem cells.

Using the PCA method, each Raman spectrum (or one or more portions) can be represented as an n-dimensional vector, where n is the number of principal components used to represent the spectrum. Each principal component is a linear combination of the original variables (i.e. channels at which Raman intensities are measured). Each vector can be broken down into one or more components, optionally an error vector can be calculated to account for variation not explained by the components. By this mathematical treatment or "decomposition," the spectrum can be represented as the weighted vector sum of the components plus the error vector. Each successive component accounts for the variation remaining in the calibration set, after subtracting the weighted contributions of all preceding components. The coefficients in the weighted sums can then be correlated with the properties of interest (i.e., type of cell, type of disease, species concentrations) using multilinear regression.

The appropriate number of components can be selected using several strategies. A common approach is to use cross-validation in which elements are left out of the data in turn. For each set of elements left out, a model is fitted to the remaining data and the model is used to estimate the left out elements. After all elements have been left out once, the thus obtained residuals are used for calculating the predicted residual sum of squares and the number of components for which predicted residual sum of squares is at its minimum is usually taken to be the appropriate number of components. Typically, it is sufficient to retain the first 2 to 6 components because these retain most of the variation. Thus, each spectrum can be decomposed to a single principal component, or it can be decomposed to 2, 3, 4, 5, or 6 principal components.

The Raman spectra or the PCA of the Raman spectra of the normal or transformed cells can be stored in a database. The Raman spectrum of an unknown cell type can be obtained, PCA can be performed on the Raman spectrum, and the principal components can be compared to data of known cell types stored in the database thereby classifying the unknown cell. In one aspect of the invention, the database containing the PCA of the Raman spectra of the known cell types is a flat file. Preferably, the PCA of the Raman spectra of the known cell types is stored in a relational format. Such a relational database supports a set of operations defined by relational algebra. It generally includes tables composed of columns and rows for the data contained in the database. Each table has a primary key, being any column or set of columns the values of which uniquely identify the rows in the table. The tables of a relational database may also include a foreign key, which is a column or set of columns the values of which match the primary key values of another table. A relational database is also generally subject to a set of operations (select, project, product, join and divide) which form the basis of the relational algebra governing relations within the database. The relational databases, client/server environments, database servers, and networks are well documented in the technical, trade, and patent literature. For a discussion of database servers, relational databases and client/server environments generally, and SQL servers particularly, see, e.g., Nath, A., The Guide To SQL Server, 2nd ed., Addison-Wesley Publishing Co., 1995. A relational database may be implemented in different ways. In Oracle™ databases, for example, the various tables are not physically separated, as there is one instance of work space with different ownership specified for different tables. In Sybase™ databases, in contrast, the tables may be physically segregated into different "databases."

A number of computer platforms can be used to perform the necessary calculations for various algorithmic processes employed in the data processing process discussed above. The system includes conventional components such as a processor, memory, disk storage, network connection, and an operating system and the like. It also includes a web browser application (e.g., Microsoft Internet Explorer, Netscape Navigator, or Opera Web Browser) to access the Internet. For example, a number of computer workstations from a variety of manufacturers can be used. In particular, workstations produced by Silicon Graphics, Inc. (SGI) of Mountain View, Calif. and multiprocessor (e.g. 12 processor) Alpha™ systems manufactured by Digital Electronics Corporation (DEC) of Maynard, Mass. have been found to be suitable for performing such calculations. The client machine may be, for example, a Macintosh™ (Apple Computer Inc. of Cupertino, Calif.), a PC, or a Unix workstation.

The cells identified as being not normal can be destroyed. For example, the laser used for optical trapping can be used to kill the cell, such as, for example, by increasing the power output, changing the wavelength of the laser where it is lethal to the cell, and the like. In another aspect, the cells identified as being not normal can be sorted from the normal cells, similar to fluorescence flow cytometry. For example, after spectral analysis, the laser used for the optical trap can be used to push the normal cells into a container for normal cells, while the abnormal cells can be pushed into a separate container. The normal cells can be returned back to the subject, whereas the abnormal cells can be removed or sorted. In another example, cells from a subject can be subjected to the above analysis in real time. In addition, a single cell can be analyzed for its real time response to various chemicals (e.g. chemotherapeutic agents).

The methods described above can be used for sorting cells, including stem cells, such as embryonic stem cells or adult stem cells. The umbilical cord from a newborn generally contains blood which is rich in stem cells. The cord blood material is usually discarded at birth, however, cord blood can be used for either autologous or allogenic stem cell replacement. Enrichment of the cord blood stem cells by optical trapping, characterization by Raman spectra, and sorting based on the analysis allows for a smaller amount of material to be stored, which can be more easily given back to the patient or another host. Adult stem cells from heart, liver, neural tissue, bone marrow, and the like, have small subpopulations of immortal stem cells which may be manipulated ex vivo and then can be reintroduced into a patient in order to repopulate a damaged tissue. The methods described above can be used to purify these extremely rare adult stem cells so that they may be used for cell therapy applications.

In another aspect of the inventions, the methods described above can be used for the detection, identification and/or quantification of single cell organisms, such as, for example, bacteria, yeast, and the like. In particular, the methods can be used for the detection of organisms of specific bacterial genus, species or serotype, in isolated form or as contaminants in environmental or forensic samples, or in foodstuff. A wide variety of single cells can be assessed with the inventive methods. These include for example gram-positive bacteria, gram-negative bacteria, fungi, viruses, gram-positive cell wall constituents such as lipoteichoic acid, peptidoglycan and teichoic acid, gram-negative endotoxin, and lipid A. Thus, the methods described above can be used to trap and identify single cells, including *Staphylococcus aureus, Listeria monocytogenes, Bacillus cereus, Salmonella*, Cholera, *Campylobacter jejuni, E. coli* and pseudomonads. It will be seen by those skilled in the art however that other types of cells can be identified using the methods described above.

The detection of single cell organisms can be used, for example, for an early diagnosis of patients suffering from a bacterial or mycotic attack of the system and thus an improved possibility of therapy can decisively improve the chances of survival. Thus, according to the present invention, there is provided a process for the detection of pathogens in the blood, such as bacteria, fungi and viruses, wherein the pathogen is separated using laser trapping, whereafter the pathogen is detected using confocal Raman spectroscopy. The Raman spectra obtained can be analyzed as described above using statistical methods and PCA. Further, the harmful cell, upon its detection, can be selectively destroyed. For example, the laser used for optical trapping can be used to kill the harmful cell, such as, for example, by increasing the power output, changing the wavelength of the laser where it is lethal to the harmful cell, and the like. In another aspect, the harmful cells identified as such can be sorted from the normal cells, similar to fluorescence flow cytometry. The methods described above can be used for the detection of sepsis. Sepsis is a serious and potentially lethal pathological condition of the body resulting from the presence of infectious microorganisms. This condition clinically manifests as one or more of the following sequelae: pyrexia (fever), hypotension (low blood pressure), hypoxemia (low blood oxygen tension), tachycardia (elevated heart rate), hypothermia (decreased body temperature), neutrophilia (increased numbers of circulating neutrophils), and neutropenia (decreased numbers of circulating neutrophils). The methods described above can be used to indicate the presence of microbial responsible for sepsis, and if present, the harmful bacteria can be destroyed thereby preventing sepsis.

In another aspect, the methods described above can be used for characterizing biologically important molecules, such as, for example, lipoproteins. Lipoproteins are typically ten nanometer to one micron diameter lipid particles found in blood that are responsible for the transport of fatty acids and cholesterol. Lipoproteins consist of a monolayer shell of phospholipids, cholesterol, and apoproteins enveloping a hydrophobic core of triglycerides and cholesterol esters. Triglyceride-rich lipoproteins (TGRL) in blood can be generated from an exogenous pathway (chylomicrons) and an endogenous pathway (very low-density lipoproteins; VLDL). The lipoprotein particles are known to penetrate the arterial wall and become trapped, initiating the early stages of atherosclerotic lesions. Therefore, acquiring information on the structure of lipoprotein particles in the pre- and postprandial states, as well as changes due to interactions with enzymes expressed on endothelial cells, can assist in elucidating the pathogenesis of atherosclerosis.

Previous studies using postprandial TGRL have primarily used standard ultracentrifugation and biochemical analysis techniques of bulk samples. These types of studies investigate entire populations of lipoproteins at a time and are therefore not specific to chemical differences between individual particles. The methods and apparatus described above allow for the non-invasive, non-destructive analysis of individual TGRL in their native environment, and can provide detailed information about the biochemical composition and biochemical changes from single lipoproteins undergoing lipid metabolism.

Any of the TGRL particles, such as VLDL, can be analyzed using the methods described above. For example, pre- and postprandial particles from human subjects consuming different diets can be chemically characterized at different points in time during the postprandial state. Biochemical changes in VLDL undergoing in situ hydrolysis during exposure to lipoprotein lipase (LpL) can be determined where in situ hydrolysis simulates the repeated lipolysis of lipoprotein particles by lipoprotein lipase anchored to the endothelial cell layer of blood vessels. To date, no studies have analyzed the composition and biochemical changes of individual plasma-derived lipoprotein particles undergoing lipoprotein metabolism and investigated the statistical variations in the composition from particle to particle. However, using the methods described above, the unique and highly reproducible bio-molecular Raman spectroscopic fingerprint of individual VLDL can be used to monitor biochemical changes of the individual particles due to lipoprotein metabolism.

V. Kits

In one aspect of the invention, an apparatus for optically trapping a single cell, obtaining its Raman spectrum, and hardware and software for analyzing the spectrum and characterizing the cell, as described in detail above, is provided. The apparatus comprises a compact low-cost diode laser that is portable, robust, and reliable. Optics and filters present the laser light to the sample and collect the Raman signals from the sample. The optics can be fiber optics for increased compactness. The system can also comprise an inverted and phase contrast microscope, CCD camera, compact fiber based spectrometers, computer, software, and a flow cell sample collection system. The computer and the software may be automated to obtain the Raman spectrum from the sample, perform PCA on the spectrum, and compare the results to the database to characterize the cell.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

An individual Raman spectrum of a cell was acquired on a CCD chip comprised of 1340 individual channels. All spectra were calibrated using a toluene solution at room temperature as standard. Raman spectra were collected within the spectral region from approximately 600 to 1800 $cm^{-1}$. Spectra were background corrected by subtraction of a $3^{rd}$ order polynomial fit via an automated routine written using Igor Pro (Wavemetric, Inc.) software. Background subtraction ensures that the baseline is the same for all cell spectra. Individual spectra were then normalized with respect to the total area under the Raman curve. The spectra from each cell type were averaged individually, by channel, to obtain a mean Raman spectrum of that particular cell type. The standard deviation was calculated for each of the 1340 channels to determine cell-to-cell variability within a particular cell type. Same-channel differences between cell-type spectra were defined using the Student's T-test statistic. Subsequently, a principal component analysis (PCA) was performed on all spectra in order to extract persistent features of spectra from individual cell classes and to compare different cell classes against each other.

Example 1

Figure 2:
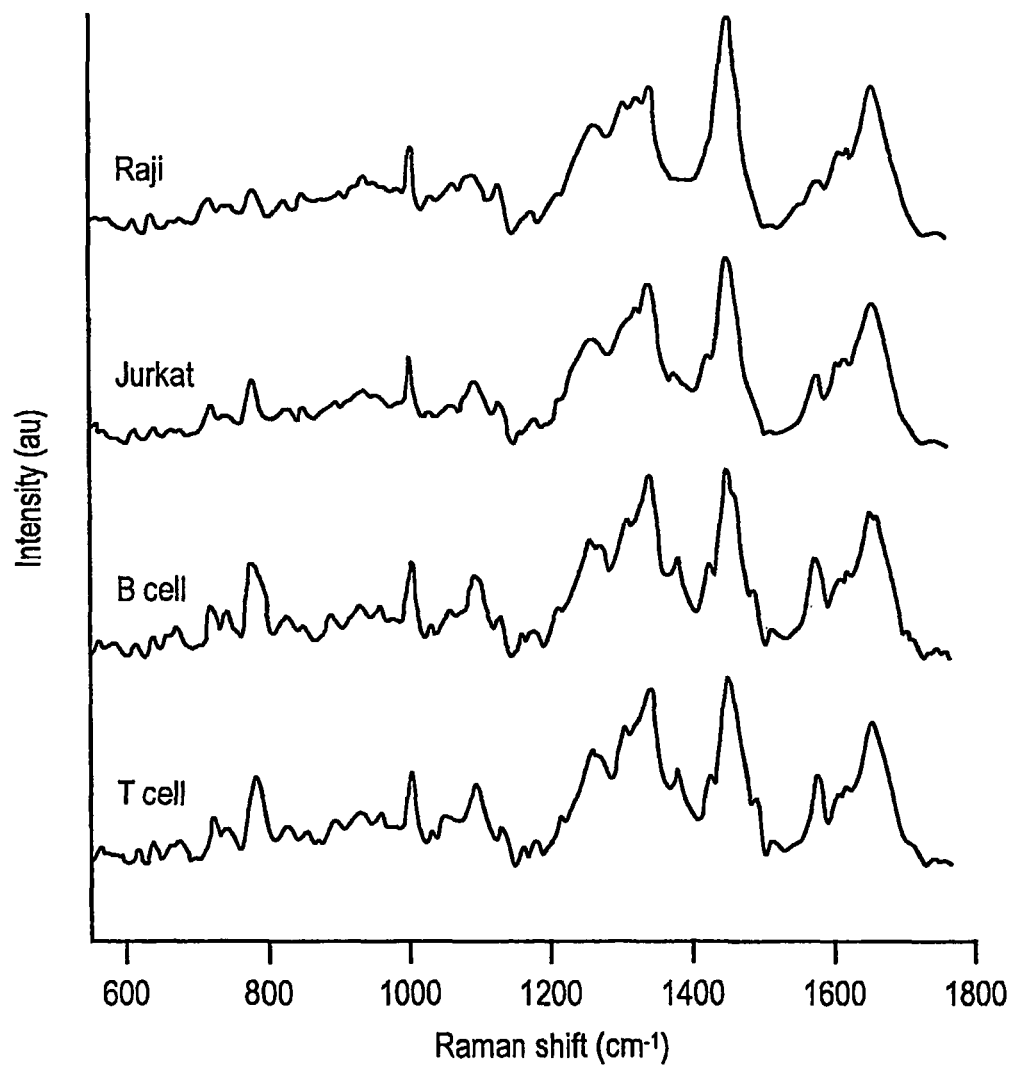
FIG. 2 illustrates the Raman spectrum of human T cells, human B cells, Jurkat T cells, and Raji B cells.

FIG. 2 shows the Raman spectrum of four different cell types, human T and B cells isolated from a patient's blood and Jurkat T and Raji B cultured cells. The Jurkat and Raji cells could not be trapped within the laser focus because of its size but were instead allowed to settle onto the glass substrate before probing with the confocal microscope. Each spectrum is an average Raman spectrum of many individual spectra from different sampled cells. The inset spectrum shows a typical Raman spectrum obtained from a single live cell acquired with a 3 minute integration time and an average laser power of 8 mW at the laser focus using a 100× oil immersion objective and a 633 nm Helium-Neon laser. The Raman spectra from all four cell types exhibit peaks that can be assigned to cellular constituents (DNA/RNA, proteins, lipids, carbohydrates). Briefly, the peaks associated with nucleic acid bases are located at 669, 725, 747, 780, 1255, 1337, 1374, 1422, 1484, 1510, and 1575 $cm^{-1}$. DNA peaks associated with the phosphate backbone occur at 788, 828, 897, and 1095 $cm^{-1}$, attributed to the $PO_2$ stretch and O—P—O stretch in the DNA backbone. Peaks at 1659 $cm^{-1}$ and 1258 $cm^{-1}$ and 1304 $cm^{-1}$ correspond to the protein amide I alpha helix and the amide III b sheet, while tryptophan peaks occur at 1617, 725, 747 $cm^{-1}$. Phe peaks are at 1603, 1176, 1033, 1003, 620 $cm^{-1}$. Tyr peaks are at 1607, 1176, 853, 828 $cm^{-1}$.

Example 2

Figure 3:
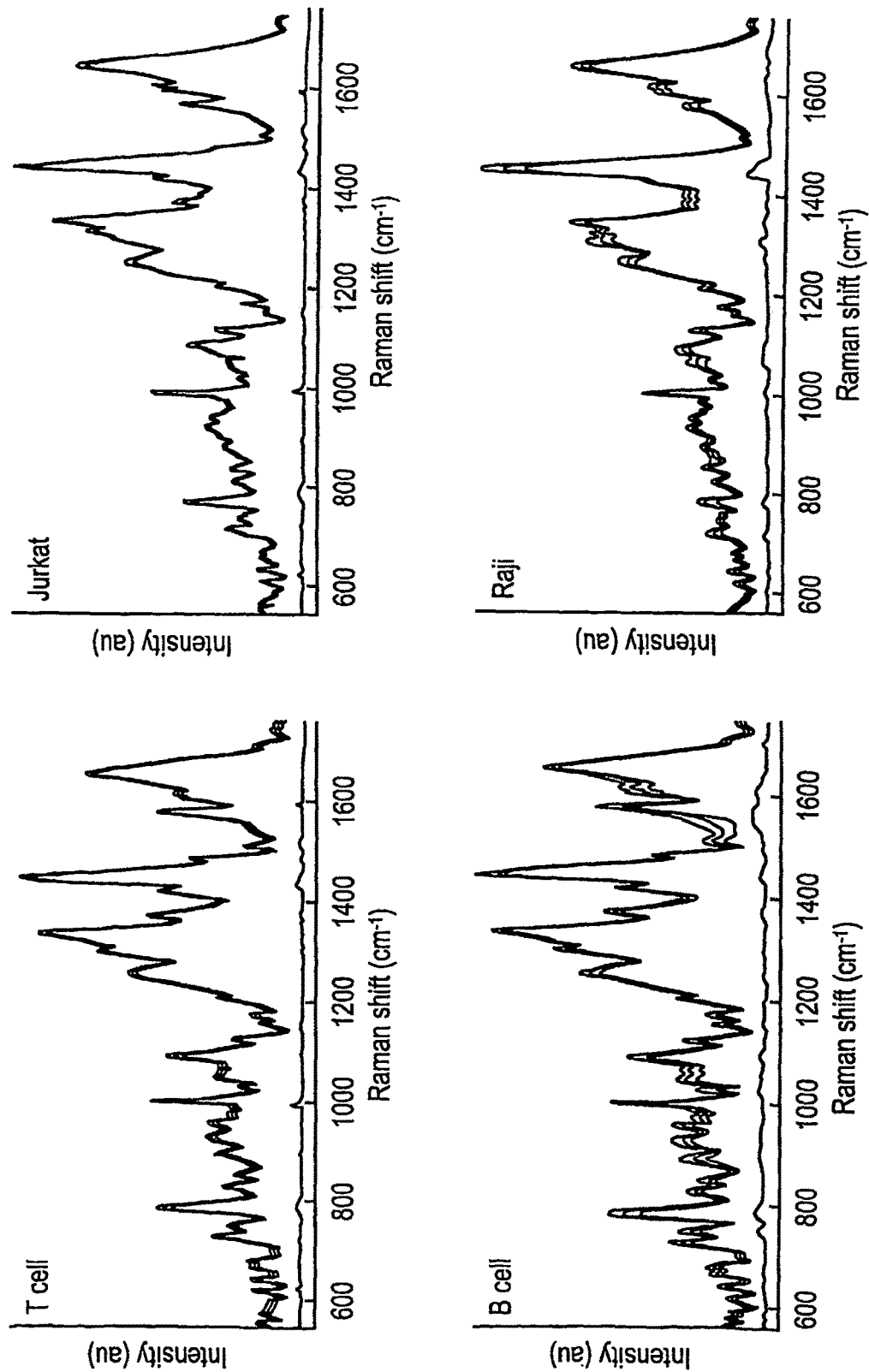
FIG. 3 illustrates the average Raman spectrum of human T cells, human B cells, Jurkat T cells, and Raji B cells and the upper and lower 99% confidence intervals for each of the channels.

The spectral variability from cell to cell within a given cell type was established to determine the accuracy of using Raman spectroscopy to positively identify an unknown cell based on its "molecular fingerprint" spectrum. To accomplish this, cell-to-cell variability for each of the four cell types was estimated by computing the 99% confidence limits for each of the 1340 channels that make up the Raman spectra. FIG. 3 are plots showing the average Raman spectrum for each cell type and the upper and lower limit Raman spectra bordering the mean spectra as determined by the 99% confidence intervals of each channel. Also shown below the Raman spectra is the variation in the calculated 99% confidence intervals, which show a flat profile with low variations except in certain Raman peaks. The plots indicate that when sampling a number of cells in a cell population, the overall variability in the acquired spectra is low and high reproducibility of the spectral features from cell to cell can be achieved, indicating that the acquired Raman spectra is a reliable fingerprint of the specific cell for positive cellular identification. The "variability index" is defined as the 99% confidence limit divided by the mean value for each of the 1340 channels that make up the Raman spectrum. The average variability index for each channel is 14.3%, 15.8%, 7.2%, and 12.9% for the T cell, B cell, Jurkat, and Raji cell groups, thus showing the high reproducibility of the data for all the cells.

Confidence T cell=avg 4.29e-5 stdev 1.6e-5, confid 1.12e-6

B cell=avg 7.98e-5 stdev 3.78e-5, confid 2.66e-6

Jurkat avg 2.97e-5, stdev 1.43e-5, 1e-6

Raji avg 7.12e-5, stdev 4.39e-5, confid 3.09e-6

Example 3

Figure 4:
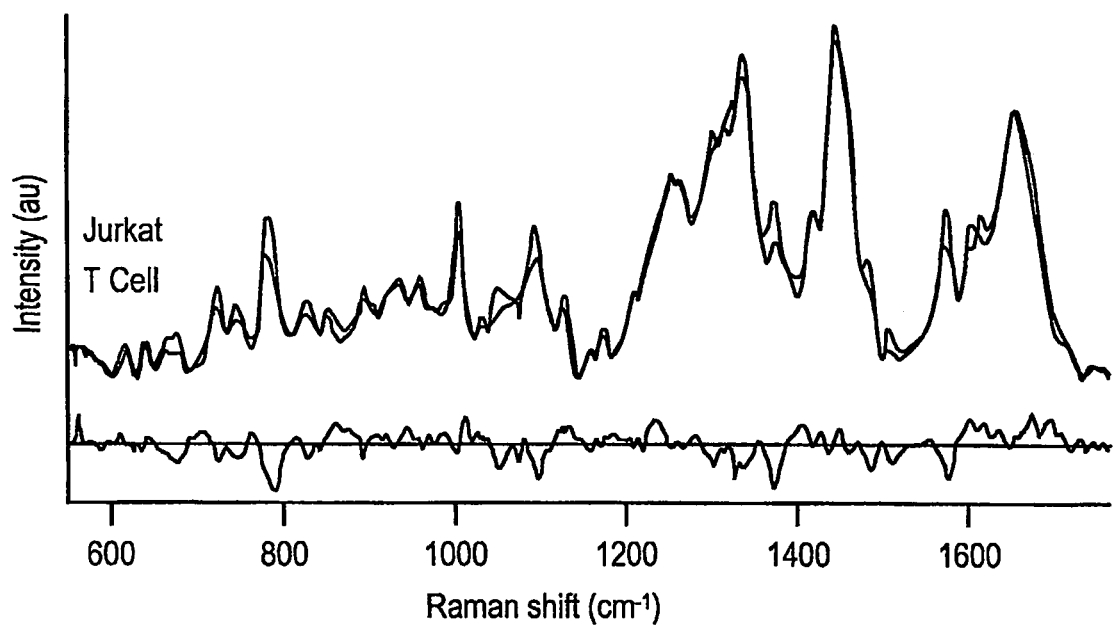
FIG. 4 illustrates the Raman spectra of normal and neoplastic T cell where the mean Raman spectra of the cells are overlapped, and the subtraction of data in each channel are plotted below.
Figure 5:
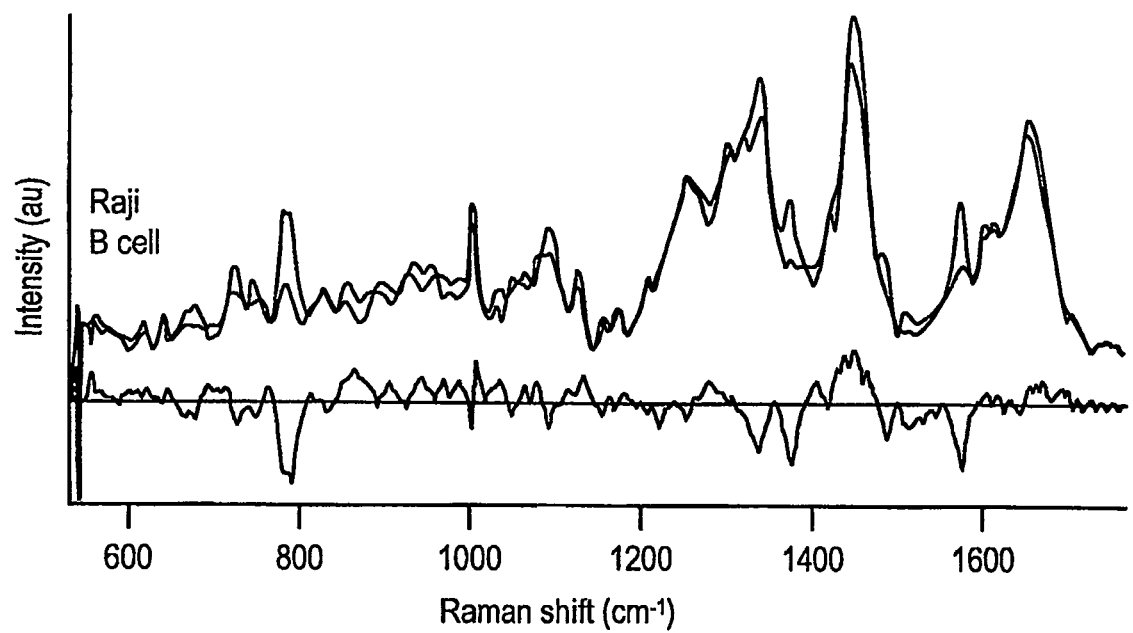
FIG. 5 illustrates the Raman spectra of normal and neoplastic B cell where the mean Raman spectra of the cells are overlapped, and the subtraction of data in each channel are plotted below.

The four sets of cells (T, B, Jurkat, Raji) characterized in Example 2 were used as a model system for comparing and identifying optical signatures in the Raman spectra thereby distinguishing between normal and neoplastic hematopoietic cells. For ease of comparison, the mean Raman spectra of the T and B cells have been overlapped with their neoplastic counterpart (Jurkat and Raji) and are shown in FIGS. 4 and 5, respectively. Qualitatively, there are clear, consistent differences between the normal and cancer cells for both cell types. For example, decreases in the 785, 1046, 1090, 1332, 1370, 1511, 1576 $cm^{-1}$ peaks and increases in the 1602 $cm^{-1}$ and 1619 $cm^{-1}$ peaks in the neoplastic cell spectra are observed.

A quantitative analysis of the differences was done by performing a t-test on the spectra to isolate those channels that have the highest significance (p<0.01). These channels were identified to be 678 $cm^{-1}$, 785 $cm^{-1}$, 1093 $cm^{-1}$, 1126 $cm^{-1}$, 1337 $cm^{-1}$, 1373 $cm^{-1}$, 1447 $cm^{-1}$, 1485 $cm^{-1}$, 1510 $cm^{-1}$, and 1575 $cm^{-1}$. A plot of the normalized intensity from these channels for all the sampled cells along with the mean value and standard deviations (see paper) shows that these values are significantly different and can be definitively used to distinguish leukemic cells from healthy normal cells.

Most features of the Raman spectra of normal T and B cells are very similar, but quite distinct from those of Raji and Jurkat cells, which in turn are both quite similar if compared against each other. Peaks that are almost exclusively due to ring breathing modes in the DNA bases, such as the modes at 678 $cm^{-1}$, 785 $cm^{-1}$, 1337 $cm^{-1}$, 1373 $cm^{-1}$, 1485 $cm^{-1}$, 1510 $cm^{-1}$, and 1575 $cm^{-1}$ are significantly reduced in intensity in Jurkat and Raji spectra. These reduced peak heights indicate that the overall DNA concentration in the probe volume of the laser beam is significantly lower in transformed cells than in normal cells. This is further confirmed by the similarly reduced intensity of the 1093 $cm^{-1}$ mode of the symmetric $PO_2^-$ stretching vibration of the DNA backbone. Some peaks that are due to protein vibrations, however, are significantly stronger in intensity in transformed cells. This is the case for the 1126 $cm^{-1}$ C—N stretching vibration, and the 1447 $cm^{-1}$ $CH_2$ deformation mode, which indicates a higher protein concentration in transformed cells than in normal cells. If the 1447 $cm^{-1}$ mode is used as a marker mode for the protein concentration, and the 1093 cm$^{-1}$ phosphate backbone vibration as a marker mode for the DNA concentration, then the relative protein-to-DNA ratio in Jurkat cells is 52% higher than in T cells, while it is 28% higher in Raji than in B cells. Between B and T cells, the ratio is almost identical (2% higher in B cells), while there is still a significant difference between Jurkat and Raji cells (17% higher in Jurkat than Raji). In comparison, the phenylalanine mode at 1003 cm$^{-1}$ stays nearly constant for all cell types, but shifts slightly to higher wavenumbers (1004 cm$^{-1}$) in the transformed cells, probably due to a somewhat different protein composition (different amino acids right next to phenylalanine) for the majority of proteins in Jurkat and Raji cells. The transformed cells and the normal cells can be distinguished by the presence of slight shoulders in their spectra at 813 cm$^{-1}$ and 1240 cm$^{-1}$. These are the positions of the two most distinct peaks for RNA and might indicate a slightly elevated concentration of RNA in the transformed cells vs. the normal cells. Other distinct RNA modes, such as the ribose vibrations at 867 cm$^{-1}$, 915 cm$^{-1}$, and 974 cm$^{-1}$ are too weak to contribute to the spectra in the present experiments. Thus, the Raman spectra of individual transformed and normal cells indicate significantly lower DNA concentrations and higher protein concentrations in transformed cells with potentially higher RNA concentrations.

Example 4

Principal Component Analysis (PCA) was used to reduce the large amount of spectral information contained in the Raman spectra into two to three principal components. A scatter plot generated from this data transformation shows clusters of points representing different cell groups, a graphical representation that is similar to results observed from flow cytometry analysis.

Figure 6:
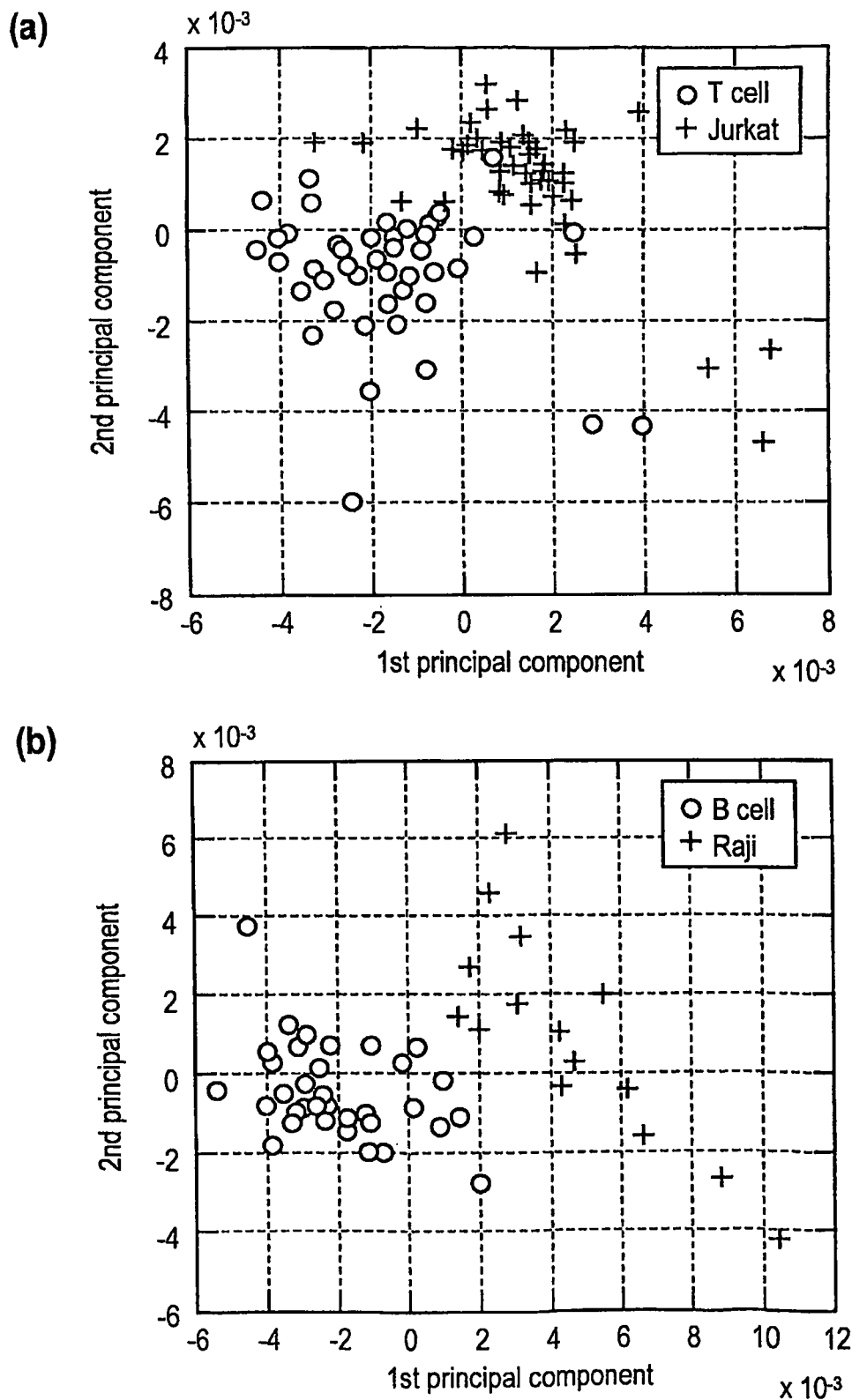
FIG. 6 illustrates Principal Component Analysis of all individual spectra of Raji, Jurkat, T, and B cells.
Figure 6A:
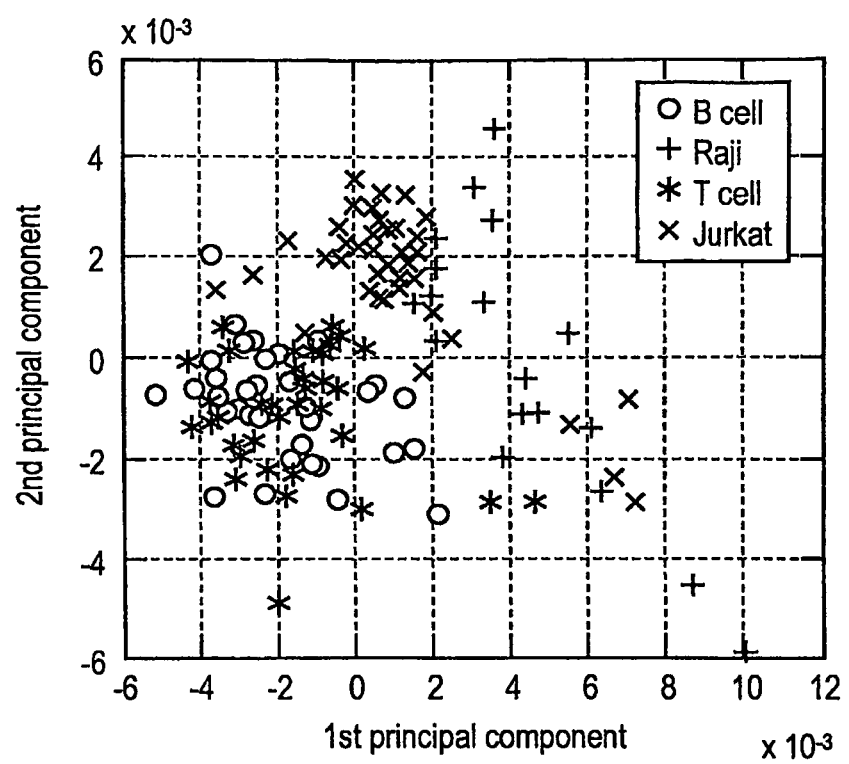
FIG. 6a shows a plot of the first principal component (PC1) v. the second principal component (PC2) for Jurkat cells and T cells.

Principal component analysis comparing normal and Jurkat T-cells (FIG. 6a) used only the first and second principal component values for the two axes and shows that the two cell types form distinct, separate clusters, where normal T-cells form one cluster and Jurkat T cells form the second cluster. PCA reveals two outlier values from the normal T-cell population within the Jurkat cluster and a small border area between the two clusters. Application of the 3$^{rd}$ principal component, that accounts for 8.3% of the variance, as a third axis of a 3-D plot did not alter this result (data not shown). The sensitivity of this technique for identifying transformed cells is calculated to be 97.8%, with a Jurkat T cell specificity of 95.5%. The total number of cells correctly classified is 96.7%. FIG. 6a contains outlier cells that are not correctly classified. One possible explanation is that the purification procedure used to isolate the normal lymphocyte populations provides samples wherein there may be 2-5% contamination with other mononuclear cells. The positive identification of these outlier cells requires real-time analysis of the acquired Raman spectra data and micromanipulation of the individual cell after data acquisition. Alternatively, the outlier cells may represent individual T-cells that are activated and progressing through the cell cycle such that they appear similar biologically to a transformed Jurkat T-cell.

PCA analysis with the two B cell groups (Raji and normal B, FIG. 6b) using only the first two PCs yields a similar plot that also forms two distinct clusters. The analysis correctly classifies all cell types into their respective cluster, indicating a sensitivity of 100%.

The simultaneous analysis of all four cell types (FIG. 6c) shows that PCA can separate the cell types into two clusters corresponding to normal and transformed cells. The sensitivity for cancer detection is 98.3%, with specificity of 96.3%. Overall, 97.2% of the cells were correctly classified as being normal or transformed cells.

Figure 7:
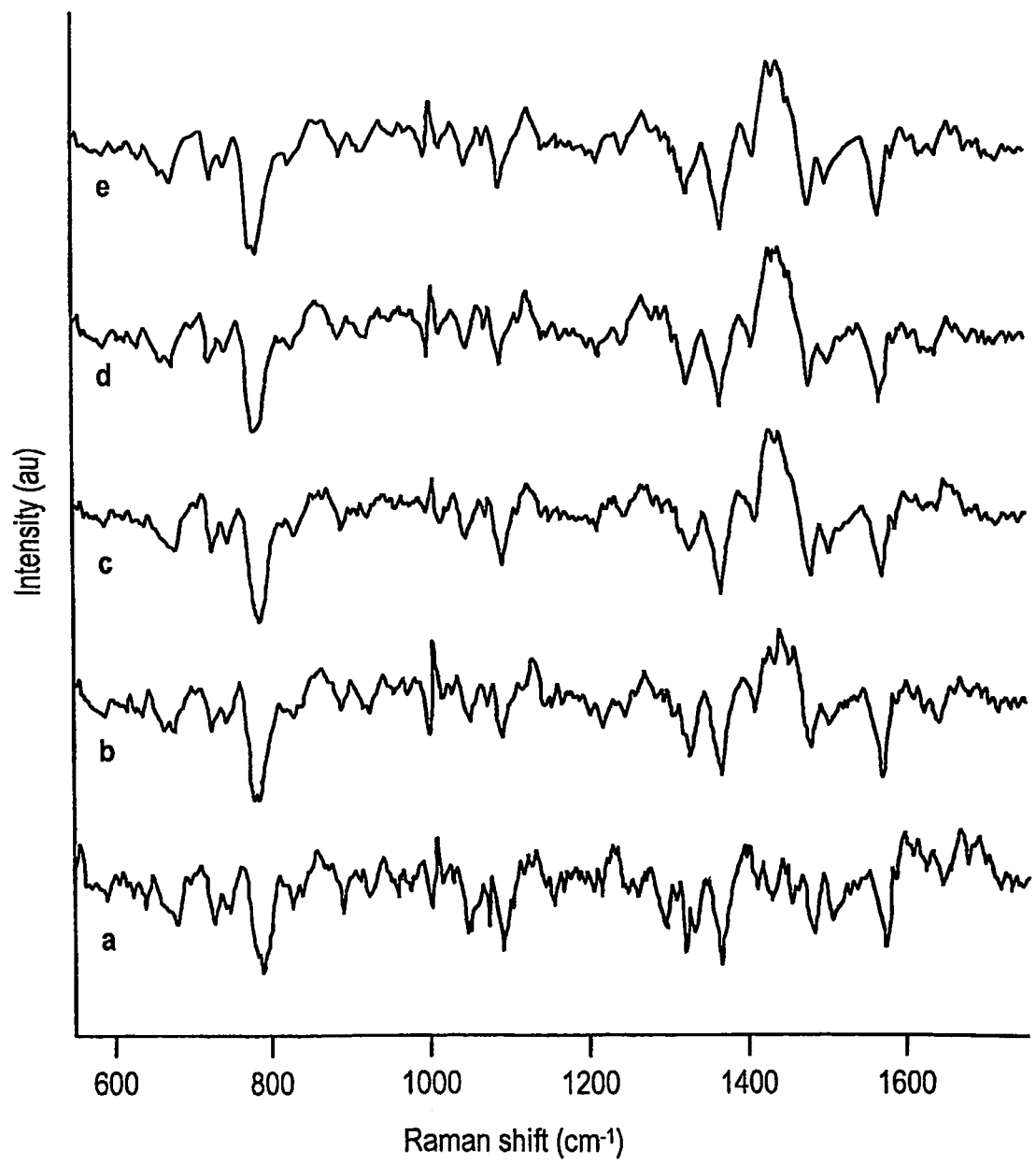
FIG. 7 compares the loading value of each channel to the $1^{st}$ PC for each comparison presented in FIG. 6 with the difference spectra shown in FIGS. 4 and 5.

Across all three PC plots, it is clear that principal component 1 (x-axis) alone provides the majority of the cluster separation. Biochemical interpretation of the differences between normal and transformed cells can also be extracted/inferred from the PC1 loading values (FIG. 7c,7d,7e) by comparing them to the difference spectra in FIGS. 4 and 5. For all the cell types analyzed by the methods described above, the major contribution to the 1$^{st}$ PC was from channels associated with DNA, RNA and protein concentration differences between cells types. This indicates that PCA is able to detect the same DNA, RNA and protein differences that were identified in the difference spectra and reduce this information into a single principal component value PC1. Thus, Raman spectroscopy provides a novel, non-destructive means that allows for biological discrimination between normal and neoplastic/transformed cells.

Example 5

Individual lipoproteins were isolated, visualized, chemically characterized, and analyzed in an entirely noninvasive fashion using the methods described above.
a. Preparation of TGRL Samples Blood was obtained from human female volunteers participating in a clinical nutrition research study examining postprandial lipemia in response to meals with low and high glycemic loads. The study was approved by the Human Subjects Research Committee of the University of California, Davis, Calif. All volunteers were overweight with BMI 27-29 and between 24-35 years of age. For 3 days prior to blood collection, volunteers consumed controlled diets with sufficient calories to match their individual energy requirements (2000-2200 kcal/d) and moderate fat content (30%). Fasting blood was obtained after a 12-h overnight fast. For the postprandial studies, volunteers consumed controlled mixed meals containing 30% total fat, 15% protein, and 55% carbohydrate. The mixed meal with the low glycemic load contained carbohydrates from whole grain products and a polyunsaturated:saturated (P:S) fat ratio of 0.2, whereas the high glycemic load meal contained carbohydrates from refined grain products and P:S ratio of 0.10. Postprandial blood was drawn at 3.5 and 8 h following meal ingestion. Blood was collected in 10 ml vacutainer tubes filled with streptokinase (150 units/ml blood). Whole blood was then spun at 4° C. for 10 minutes at 1750 g, to remove cellular particulate. After centrifugation, plasma was transferred to ultracentrifuge tubes (Beckman-Coulter) and centrifuged at 285,000 g at 4° C. for 4 hours to isolate TGRL. This procedure removes all higher density lipoprotein particles (LDL, HDL, and IDL) with a diameter of less then 40 nm. After ultracentrifugation, TGRL was removed and the concentration was measured using an Infinity Triglyceride Concentration kit (Sigma Diagnostics). The final samples containing only chylomicrons, VLDLs and their remnants were stored on dry ice and then transported to LLNL. The plasma was diluted 1:100 in PBS buffer to separate and isolate individual TGRL in buffer solution. Analysis of the TGRL by LTRS was typically conducted no later than 48 hours after extraction.
b. Acquisition of Raman Spectra of Single Optically Trapped TGRL The LTRS system consists of a 632.8 nm CW laser beam spectrally filtered with a 633 nm bandpass filter and delivered into the back port of a Zeiss Axiovert 200 inverted microscope. A longpass dichroic reflector directs the beam through a 100×, 1.3 NA oil immersion objective (Zeiss), resulting in a diffraction limited spot of roughly 0.5 µm diameter with 10 mW laser power. The tight focus creates an optical trap that immobilizes single TGRL particles drifting in the plasma solution. White light illumination in transmission was used to obtain images captured on a CCD video camera. Epi-detection of the Raman signals of the trapped particle is achieved using the same objective and a 100 µm pinhole in a confocal arrangement. The signals were filtered using a holographic 633 nm notch filter for suppression of residual laser light, directed into a spectrometer equipped with a 1200 lines/mm grating, blazed at 500 nm, and focused onto a liquid nitrogen cooled CCD camera (1340×100 pixels). Optical trapping of single TGRL particles was accomplished by using the translation stage to move the particles to a close proximity of the laser focus, at which point the particle was drawn into the focus and then trapped. A typical acquisition time of 60 seconds was sufficient to acquire a Raman spectrum of typically better than 10:1 signal-to-noise ratio with clearly defined Raman bands. Spectra were calibrated to a toluene standard and background correction was performed on each spectrum by subtraction of a $3^{rd}$ order polynomial baseline fit. Each spectrum was normalized to the intensity of the 1440 $cm^{-1}$ peak because fluctuations due to changes in protein concentration or conformation are relatively weak. The differentiation of the differently sized TGRL (large vs. small) was based on their visibility in the optical microscope by comparison to polystyrene beads of well-known size.

c. Acquisition of Raman Spectra from Unsaturated and Saturated Oils

Cis-9-octadecenoic acid (oleic acid), hexadecanoic acid (palmitic acid) and octadecanoic acid (stearic acid) oil standards with purity greater than 95% were purchased from Sigma. The saturated fatty acid samples (palmitic acid and stearic acid are solid at room temperature. To simulate the effects of carbon chain disordering, samples of palmitic and stearic acid were also heated above their melting point in a water bath. The samples were examined at room temperature and ~70° C., respectively, by placing either the powder (palmitic and stearic acids at room temperature) or liquid (oleic acid; palmitic and stearic acid heated above the melting point) on a calcium fluoride substrate. A 20× long working distance objective was used to focus the 633 nm laser beam onto the samples. Spectra were acquired with a 30 second integration time.

d. Hydrolyzation of TGRL Particles with Lipoprotein Lipase (LpL)

Figure 9:
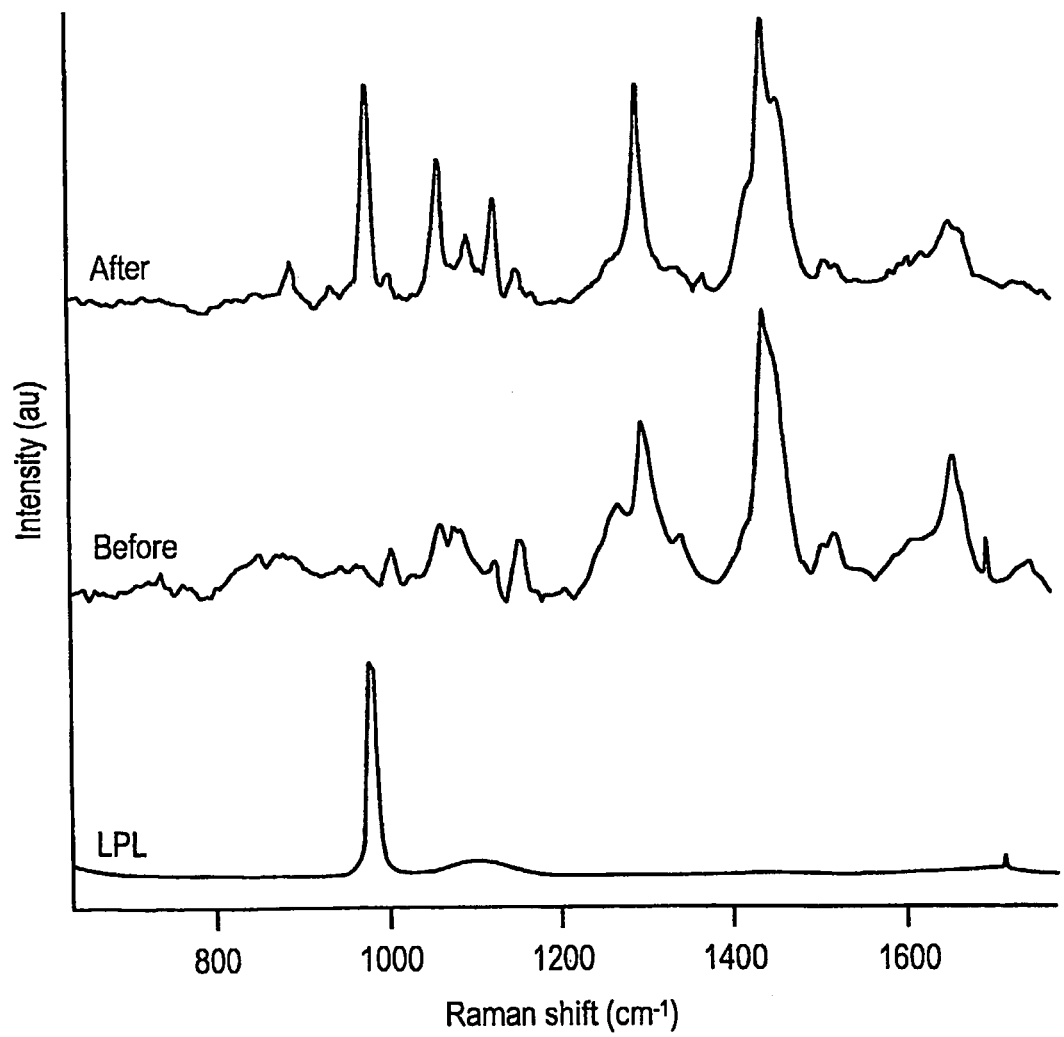
FIG. 9. Individual Raman spectra of TGRL particles before and after 1 hour exposure to lipoprotein lipase. The Raman spectrum of lipoprotein lipase is also shown.

Lipoprotein lipase from bovine milk, (diacylglycerol acylhydrolase), was purchased from Sigma. 15 µL of the enzyme is added to approximately 1 mL of TGRL particles in plasma solution in an Eppendorf tube, with a density of 400 mg/dL. This results in a concentration of $1.4×10^2$ mg/mL (74 total units) of enzymatic proteins. Spectra of many particles were taken both before and 60 minutes after addition of the LpL. FIG. 9 shows a sample spectrum of individual particles before and after exposure to LpL and the background from LpL in buffer.

The results show that for particles of roughly 150 nm and larger, a single trapped TGRL at the focus can be observed by white light imaging with a CCD camera. For smaller particles (<100 nm; VLDL and remnant particles), optical trapping is still feasible with the laser power used in this study. In this case, the TGRL were detected by the Rayleigh-scattering of the laser light backscattered off the trapped particle (see the inset of FIG. 8), which can be observed after removal of the filters in front of the CCD camera.

Figure 8:
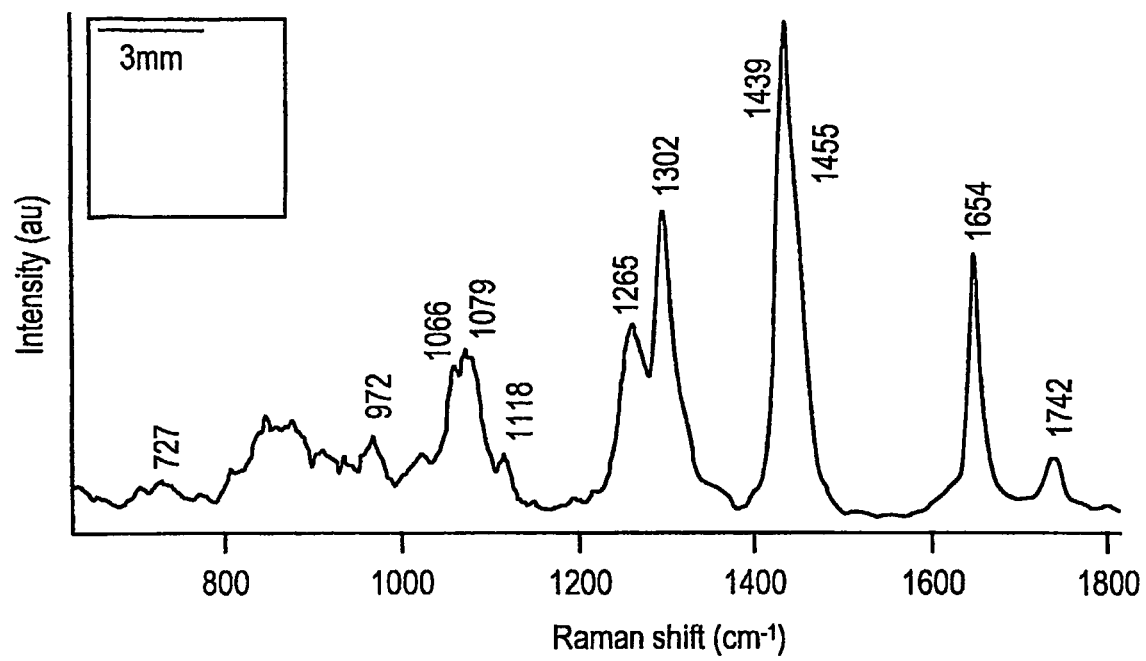
FIG. 8. Raman spectrum of a single optically trapped TGRL particle taken with 10 mW laser power for 60 seconds (see table for peak assignments). A particle is confirmed to be trapped by detection of the backscattered laser light off the particle at the focus (see inset).

A typical background-corrected and normalized Raman spectrum of a single trapped TGRL particle is shown in FIG. 8. This spectrum was obtained from a VLDL particle in plasma from a volunteer who consumed a controlled diet with moderate fat content (30%) for 3 days and then fasted for 12 hours prior to sample extraction. We call this a 0 hr sample, because it was obtained before the volunteers consumed a meal. The spectrum was obtained with a 60 second signal accumulation time using 10 mW of 633 nm laser power and shows a rich vibrational structure. The major peaks and their assignments are listed in Table I.

TABLE I

Raman frequencies of individual TGRL and their assignments

| Raman frequency in wavenumber units ($cm^{-1}$) | Assignment[a] |
|---|---|
| 727 | δ (=C—H) in-plane |
| 972 | δ (=C—H) out-of-plane |
| 1066 | ν (C—C) |
| 1079 | ν (C—C) |
| 1119 | ν (C—C) |
| 1265 | δ (=C—H) in-plane cis |
| 1302 | δ ($CH_2$) twisting |
| 1439 | δ ($CH_2$) scissor |
| 1455 | δ ($CH_2$) |
| 1654 | ν (C=C) cis (lipid), and ν (O—H) (water) |
| 1742 | ν (C=O) in —$CH_2$—COOR |

[a]Abbreviations: ν and δ indicate stretching and deformation vibrations, respectively. See text for more details.

The peaks observed in this 0 hour spectrum of a VLDL particle can be readily assigned to known major lipid bands by comparing them to previously published results. The peak at 727 $cm^{-1}$ is assigned to an in-plane bending mode of the C—H bond in a double bond. The 972 $cm^{-1}$ peak is an out-of-plane deformation mode of the C—H bond. The peaks at 1066, 1076, and 1129 $cm^{-1}$ correspond to C—C stretching vibrations and the 1266 $cm^{-1}$ peak is due to an in-plane C—H bending mode in a double bond. The peak at 1302 $cm^{-1}$ can be attributed to a CH2 twisting mode, the 1439 $cm^{-1}$ peak to a CH2 scissor mode, the 1654 $cm^{-1}$ peak to a C=C stretch mode (indicative of unsaturated bonds), and the 1742 $cm^{-1}$ to a C=O bond in an ester. The broad shoulder on both sides of the 1654 $cm^{-1}$ band is a background contribution from the 0-H stretching vibration of water in the plasma solution. These peaks provide information about the chemical components and conformations of the VLDL. It is known that spectra of triacylglycerol exhibit the presence of the 1742 $cm^{-1}$ peak that is lacking in spectra of free fatty acids, confirming that triacylglycerol is likely present in the core of the lipoprotein particle. The location of the 1650 $cm^{-1}$ band indicates a cis conformation in the C=C double bond, which would otherwise be located at 1668 $cm^{-1}$ for the trans conformation, and is therefore another marker for unsaturated bonds. The presence of the 1266 $cm^{-1}$ band also indicates a cis geometry.

Figure 10:
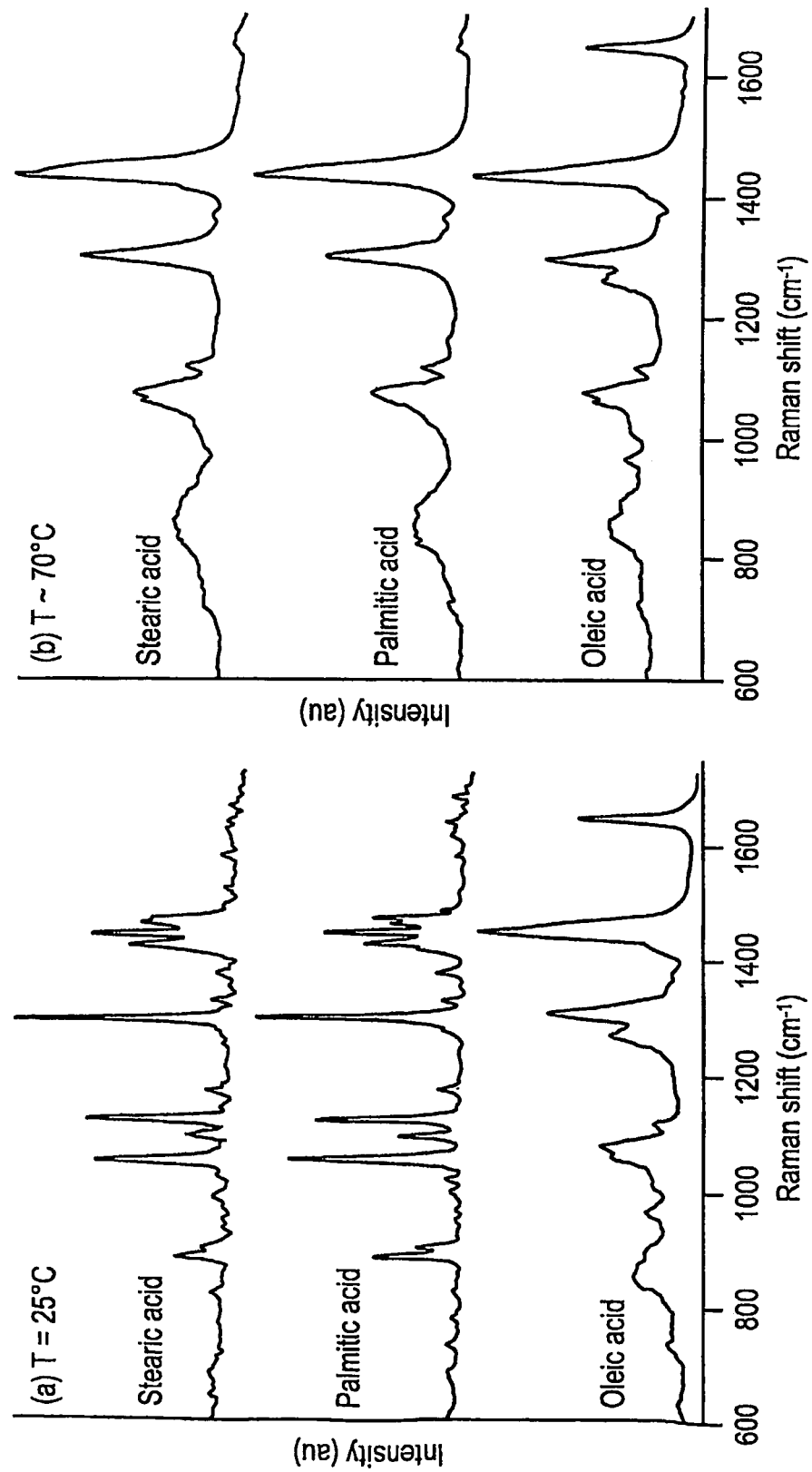
FIG. 10. Raman spectra of oleic, palmitic, and stearic acid at (a) room temperature and (b) 70° C. Saturated fatty acids (palmitic and stearic acids) at room temperature exhibit a number of unique sharp spectral peaks, e.g. at 1062, 1128, and 1296 $cm^{-1}$ that are not observed for the unsaturated oleic acids. These changes indicate highly ordered carbon chains in the saturated fatty acids, which disappear at temperatures above the melting point (b). In this case, the C=C vibrations at 1266 $cm^{-1}$ and 1655 $cm^{-1}$ become the most distinct differences between the fatty acid standards.

To aid in the characterization of Raman spectroscopic differences between VLDLs extracted at different points in time, Raman signatures of various oil standards were acquired. FIG. 10 shows the Raman spectra of three different types of fatty acids. Cis-9-octadecenoic acid is a monounsaturated fatty acid with an 18 carbon atom chain with one double bond in the cis configuration. Hexadecanoic and octadecanoic acid are both saturated fatty acids with 16 and 18 carbon atom chains, respectively. The Raman spectra of the saturated fatty acids at room temperature are noticeably different from that of the unsaturated fatty acid. Very distinct, narrow sharp peaks at 891 $cm^{-1}$, 1062 $cm^{-1}$, 1097 $cm^{-1}$, 1128 $cm^{-1}$, 1296 $cm^{-1}$, 1419 $cm^{-1}$, and 1440 $cm^{-1}$ are observed in addition to the absence of peaks at 1266 $cm^{-1}$ and 1655 $cm^{-1}$. These characteristic peaks have been previously observed and identified in saturated triacylglycerols and saturated free fatty acids probed by Fourier transform Raman spectroscopy. The peaks, specifically at 1062, 1097, and 1128 $cm^{-1}$ can be assigned to C—C stretching in a hydrocarbon chain and the 1296 $cm^{-1}$ to a CH2 twist. The intensity and relative positions of the peaks in the 1000-1150 $cm^{-1}$ region are sensitive to the conformational state of the hydrocarbon chain. The 1062 and 1128 $cm^{-1}$ vibrations have been assigned to highly ordered all-trans chain segments while the 1097 $cm^{-1}$ is associated with structures having gauche rotations. A highly disordered chain results in a broadening of the gauche band and shifts to lower frequency in addition to decreases in intensity of both the 1128 and 1063 $cm^{-1}$ bands. Therefore, the Raman spectra of palmitic and stearic acid at room temperature indicate that these fully saturated hydrocarbon chains are highly ordered while oleic acid, an unsaturated fatty acid with a carbon-carbon double bond results in chain disorder. If palmitic and stearic acid are heated above their melting point to induce disorder in the hydrocarbon chains, the sharp peaks that are assigned to highly ordered chains disappear and the spectra become more like that of oleic acid. Peaks due to unsaturated double bonds at 1266 $cm^{-1}$ and 1655 $cm^{-1}$, however, are not present. We can thus use the presence of sharp peaks in the 1000-1150 $cm^{-1}$ range as markers for highly ordered saturated fatty acids, whereas peaks at 1266 $cm^{-1}$ and 1655 $cm^{-1}$ indicate the presence of unsaturated fatty acids.

Figure 11:
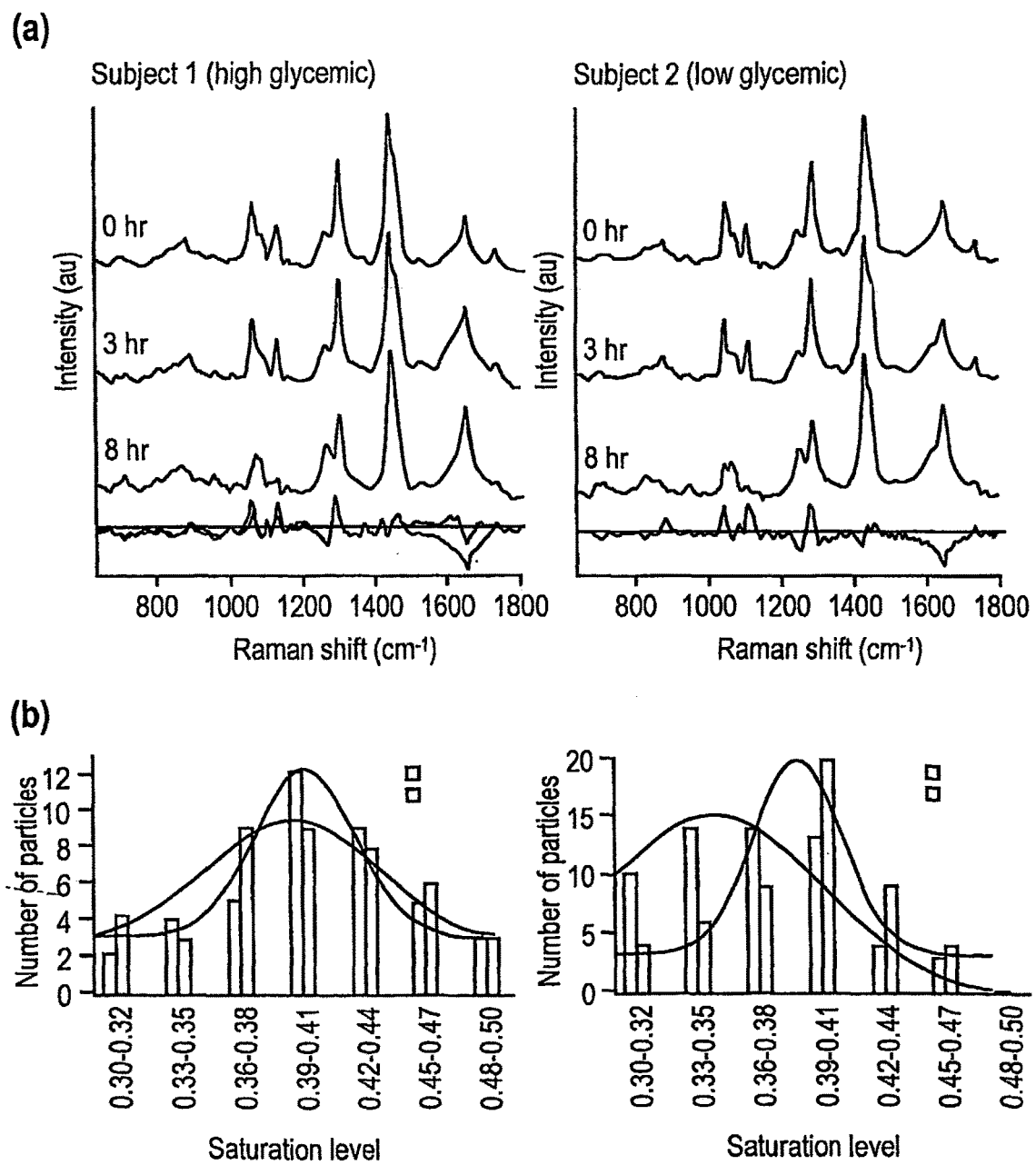
FIG. 11. (a) Averaged Raman spectra of TGRL particles extracted from human volunteers at three time intervals before and after the consumption of a meal, and the 3 and 8 hour difference spectra. (b) Plots showing the particle distribution based on the intensity of the 1060 $cm^{-1}$ peak, indicative of the concentration of highly ordered saturated fatty acids in the particles. Solid lines are fits to the particle distributions and serve only as guides to the eye.

We obtained Raman spectra of individual VLDLs obtained from volunteers at 0 hr, 3 hr, and 8 hr, respectively, after consumption of high and low glycemic load test meals. Between 20 and 30 VLDL particles were examined at each time point. All subjects were held on either high or low glycemic diets, which had been consumed for 3 days prior to the test meal. FIG. 11 shows the average Raman spectra of the particles from the three time intervals for both high and low glycemic load diets. Also shown are the 3 hr and 8 hr difference spectra after subtraction of the 0 hr spectra. The spectra clearly reveal differences in the Raman spectra at 3 hr and 8 hr after meal ingestion. Most notable are the formation of distinct, sharp peaks at 1060 and 1129 $cm^{-1}$, a decrease in the 1266 $cm^{-1}$ band, a shift and narrowing of the peak at 1298 $cm^{-1}$, an increase in the 1099 $cm^{-1}$ peak intensity, and a decrease in the 1650 $cm^{-1}$ band for both test subjects.

The 0 hr spectra for both volunteers are very similar to those obtained from the unsaturated oleic acid, thereby indicating that these VLDLs are highly unsaturated and have a relative lack of any saturated fatty acids in the core of the particle. The peaks in these Raman spectra are mainly due to vibrational signatures of the phospholipid shell in addition to cholesterol ester and unsaturated fatty acids in the particle. The results from our pre- and 3 and 8 hour postprandial study of biochemical changes in VLDL particles (FIG. 11) indicate that following meal consumption, the main biochemical changes in VLDLs are that the long hydrocarbon lipid chains in the particle adopt a higher ordered conformation, based on the observed changes in the 1000-1150 $cm^{-1}$ region. Also, peaks due to unsaturated bonds (e.g. 1265 and 1654 $cm^{-1}$ peaks associated with C=C bonds) are decreasing in intensity for the postprandial particles.

These spectral changes reveal detailed information on the biochemical changes that are occurring in the particles as VLDL is hydrolyzed through repeated exposure to LpL on endothelial cell membranes. The triacylglycerols initially present in the particle are complex molecules, where the three hydrocarbon chains may consist of combinations of very different fatty acid chains (e.g. saturated and unsaturated chains, long and short chains, unsaturated chains with double bonds in different positions). Since it is known that saturated and unsaturated chains do not preferentially mix, instead favoring the formation of separate domains, triacylglycerol molecules encounter steric problems because the covalently linked fatty acid chains are forced to pack together. Therefore, these molecules adopt highly disordered packing. Following meal consumption, the triacylglycerol molecules packed in the particle core undergo hydrolysis as the particle interacts with endothelium and are broken down to form unsaturated and saturated free fatty acids, which are now free to form separate highly ordered domains. Accordingly, increases in the peaks in the 1000-1150 $cm^{-1}$ spectral region indicate the presence of highly ordered cores of saturated fatty acids only in the 3 and 8 hour postprandial particles.

Thus, the methods described above can be used for the analysis of individual particles and their statistical distributions. As discussed above, the relative distribution of fatty acids in particles in the 3 and 8 hr postprandial states can be used to assess differences in VLDL lipolysis depending on the fat content of a meal. The normalized value of the 1060 $cm^{-1}$ Raman peak from individual particle spectra was used as a marker associated with high levels of highly ordered hydrocarbon chains, which represent saturated fatty acids at room temperature. FIG. 11b shows a distribution plot of the saturation levels (i.e. peak intensity) of particles at 3 and 8 hours for both diets. The distribution plots clearly show that the saturation levels from particle to particle vary greatly for both the low and high glycemic load meals and at different times in the postprandial period. The 3 hour postprandial particles from the low glycemic study appear to have an overall higher degree of unsaturation compared to those from the high index study. This distribution shifts to the right at 8 hours, indicating a lipolysis-related increase in free saturated fatty acids with time during the postprandial state. In contrast, the particles from the high glycemic study have a similar broad distribution at both times with no significant change in the peak position between 3 and 8 hours postprandial time. One of the main differences between the two meal types is the total saturated fat content of the low and high glycemic load test meal (16.2 g and 17.1 g, respectively). The data show that the distribution analysis of the 3 hour postprandial particles directly reflects the content of saturated fatty acids of the ingested meal, while the 8 hour postprandial particle spectra no longer reflect the saturation level of the meals. For a meal with higher content of saturated fatty acids, postprandial VLDLs contain higher amounts of saturated triacylglycerols that apparently require repeated exposure to LpL to convert them to free saturated fatty acids, which can then be detected spectroscopically.

There is a marked difference between the 8 hour spectra and the 0 hour spectra. The 0 hour spectra were obtained after a 12 hour fasting period. This indicates that the highly ordered saturated fatty acids found in VLDLs 8 hours after meal consumption are removed and converted some time between the 8 and 12 hour time frame. This process could be related to the transfer of fatty acids or triacylglyerols to other lipoprotein particles via transfer proteins. These plots demonstrate the ability of this technique to detect subtle changes and subdistributions in the composition of single particles that bulk or averaged spectral analysis cannot offer. However, additional experiments encompassing a larger set of data from many subjects are still required to draw definitive conclusions about these observed trends.

To further elucidate the effect of LpL hydrolysis on individual VLDL particles, the TGRL particles were exposed to lipoprotein lipase (LpL), an enzyme found anchored to the endothelial cell surface. Normalized Raman spectra of individual lipoprotein particles before and after exposure to lipoprotein lipase (LpL) are shown in FIG. 9. A slight decrease in the 1742 $cm^{-1}$ peak following hydrolysis was observed, indicating that the triglycerides are being converted to free fatty acids. Most notable are the formation of narrow peaks at 1060, 1097, 1129, and 1298 $cm^{-1}$ and a decrease in the 1265 and 1655 $cm^{-1}$ peaks. Since there is no pathway for the addition of saturated fatty acids during this experiment, these spectral changes are clearly not a result of increased amounts of saturated oils in the particle but rather a direct indication of the enzymatic reaction occurring between the VLDL particle and the LpL enzyme, as discussed above. These changes indicate that after hydrolysis of the triacylglycerol-containing particles, the saturated fatty acids are free to form separate domains, resulting in a particle that now consists of a core with highly ordered chains. This result is very similar to the biochemical changes observed in the postprandial particles extracted after different periods in time and confirms that we are observing biochemical changes in the native VLDL particles that are due to repeated exposure to LpL.

Thus, individual lipoproteins can be isolated, visualized, chemically characterized, and analyzed in an entirely non-invasive fashion. Moreover, ex vivo analysis of individual lipoproteins can be performed rapidly and at near-physiological conditions (TGRL in pure plasma and PBS solution). This obviates the need for long, complicated and potentially destructive lipoprotein preparation protocols. In addition, compositional changes in a single TGRL particle can be monitored as it is exposed to lipoprotein lipase, saturated fatty acids, and other lipids or proteins added to the buffer containing TGRL.

While the invention has been particularly shown and described with reference to a preferred embodiment and various alternate embodiments, it will be understood by persons skilled in the relevant art that various changes in form and details can be made therein without departing from the spirit and scope of the invention. All printed patents and publications referred to in this application are hereby incorporated herein in their entirety by this reference.

We claim:

1. A method for non-destructively characterizing a cell, the method comprising:
    providing a sample comprising at least one intact cell in a solution, wherein the at least one intact cell is a white blood cell;
    optically trapping a single intact cell from the sample using a laser using an excitation wavelength selected from the group of about 800-1800 nm, 780-950 nm, and 780-800 nm, wherein the excitation wavelength is selected to minimize the deleterious effects of heating the single intact cell;
    illuminating the single intact trapped cell with the laser to generate a Raman spectrum, wherein the laser is not deleterious to the single intact trapped cell;
    analyzing the Raman spectrum to characterize the single intact trapped cell;
    identifying the single intact trapped cell as normal or abnormal based on the analyzed Raman spectrum; and
    if the single intact trapped cell is identified as abnormal, removing the trapped intact abnormal cell from the sample using the laser.

2. The method of claim 1, wherein the white blood cell is a T-lymphocyte.

3. The method of claim 1, wherein the white blood cell is a B-lymphocyte.

4. The method of claim 1, wherein the white blood cell is a normal cell or an abnormal cell.

5. The method of claim 4, wherein the abnormal cell is a lymphoma cell.

6. The method of claim 4, wherein the abnormal cell is a leukemia cell.

7. The method of claim 4, wherein the abnormal cell is a myeloma cell.

8. The method of claim 1, wherein the Raman spectrum is stored in a plurality of channels wherein each channel stores a single wavelength.

9. The method of claim 8, wherein one or more of the plurality of channels is subjected to a statistical analysis.

10. The method of claim 9, wherein the statistical analysis comprises obtaining a 95% to 99% confidence limit.

11. The method of claim 9, wherein the statistical analysis comprises obtaining the variability index.

12. The method of claim 9, wherein the statistical analysis comprises performing a t-test.

13. The method of claim 9, wherein said statistical analysis identifies a significant channel, the method further comprising comparing the significant channel to one or more channels of a normal cell Raman spectrum, or to one or more channels of an abnormal cell Raman spectrum, or to one or more channels of both.

14. The method of claim 13, wherein the one or more channels comprise between 1 and 100 channels.

15. The method of claim 14, wherein the one or more channels comprise between 1 and 15 channels.

16. The method of claim 8, wherein the Raman spectrum is subjected to Principal Component Analysis (PCA).

17. The method of claim 16, wherein principal components are compared to principal components of a set of preprocessed spectra obtained from cells of known pathology.

18. The method of claim 16, wherein PCA includes between 2 and 6 principal components.

19. The method of claim 18, wherein PCA includes 2 or 3 principal components.

20. The method of claim 1, wherein the analyzing step comprises comparing the produced Raman spectrum to a Raman spectrum of a normal cell, or to a Raman spectrum of an abnormal cell, or to both.

21. The method of claim 1, wherein removing the abnormal cell further comprises destroying the abnormal cell.

22. The method of claim 1, wherein removing the abnormal cell comprises sorting the abnormal cell away from the sample.

* * * * *